(12) United States Patent
Stokes et al.

(10) Patent No.: US 8,247,562 B2
(45) Date of Patent: Aug. 21, 2012

(54) BENZAMIDE DERIVATIVES USEFUL AS HISTONE DEACETYLASE INHIBITORS

(75) Inventors: Elaine Sophie Elizabeth Stokes, Macclesfield (GB); Craig Anthony Roberts, Macclesfield (GB); Michael James Waring, Macclesfield (GB)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 12/879,367

(22) Filed: Sep. 10, 2010

(65) Prior Publication Data

US 2010/0331329 A1 Dec. 30, 2010

Related U.S. Application Data

(63) Continuation of application No. 12/211,510, filed on Sep. 16, 2008, now abandoned, which is a continuation of application No. 10/509,941, filed as application No. PCT/GB03/01442 on Apr. 2, 2003, now abandoned.

(30) Foreign Application Priority Data

Apr. 5, 2002 (GB) .................................. 0207863.2
Dec. 21, 2002 (GB) .................................. 0229930.3

(51) Int. Cl.
C07D 211/32 (2006.01)
C07D 401/06 (2006.01)
A61K 31/452 (2006.01)
A61P 35/00 (2006.01)

(52) U.S. Cl. ......... 546/192; 546/196; 514/317; 514/320

(58) Field of Classification Search .................. 546/192, 546/196; 514/317, 320
See application file for complete search history.

(56) References Cited

U.S. PATENT DOCUMENTS

| 3,931,215 A | 1/1976 | Horn et al. |
| 3,974,172 A | 8/1976 | Sahm et al. |
| 4,289,887 A | 9/1981 | Wehling |
| 5,232,937 A | 8/1993 | Makovec et al. |
| 6,174,905 B1 | 1/2001 | Suzuki et al. |
| 2004/0087631 A1 | 5/2004 | Bacopoulos et al. |
| 2005/0124497 A1 | 6/2005 | Fusslein et al. |

FOREIGN PATENT DOCUMENTS

| EP | 0847992 B1 | 6/1998 |
| EP | 1273575 B1 | 1/2003 |
| JP | 05239069 A | 9/1993 |
| JP | 10-152462 A | 6/1998 |
| JP | 11-269140 A | 10/1999 |
| JP | 11-269146 A | 10/1999 |
| JP | 11-302173 A | 11/1999 |
| JP | 11-335375 A | 12/1999 |
| JP | 2000-302765 A | 10/2000 |
| JP | 2002-161084 A | 6/2002 |
| WO | 01/38322 A1 | 5/2001 |
| WO | 01/74791 A1 | 10/2001 |
| WO | 03/024448 A2 | 3/2003 |
| WO | 03/075839 A2 | 9/2003 |
| WO | 03/075856 A2 | 9/2003 |
| WO | 03/075929 A1 | 9/2003 |
| WO | 03/076395 A1 | 9/2003 |
| WO | 03/076400 A1 | 9/2003 |
| WO | 03/076401 A1 | 9/2003 |
| WO | 03/076421 A1 | 9/2003 |
| WO | 03/076422 A1 | 9/2003 |
| WO | 03/076430 A1 | 9/2003 |
| WO | 03/076438 A1 | 9/2003 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Rosato et al., Expert Opin. Investig. Drugs 13(1), 21-38, 2004.*
Cecil Textbook of Medicine, edited by Bennet, J.C., and Plum F., 20th edition, vol. 1, 1004-1010, 1996.*
Ragione et al., FEBS Letters 499. 199-204, 2001.*
Freshney et al., Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141 802-810, 1999.*
Golub et al., Science, 286, 531-537, 1999.*
Andrews D.M. et al: "Design and Campaign Synthesis of piperidine- and thiazole-based histone deacetylase inhibitors", Bioorganic and Medicinal Chemistry Letters, 2008, 18, 2580-2584.
Andrews D.M. et al: "Design and Campaign Synthesis of pyridine-based histone deacetylase inhibitors", Bioorganic and Medicinal Chemistry Letters, 2008, 18, 2525-2529.
Andrews D.M. Oral small molecule anticancer lead optimization: Lessons in campaign design, synthesis and testing, 236th ACS National Meeting, Philadelphia, PA, Aug. 17-21, 2008 (2008), (Lecture given on Aug. 21).
Cecil Textbook of Medicine, edited by Bennet, J.C., and Plum F., 20th edition, vol. 1, 1004-1010, 1996.

(Continued)

Primary Examiner — Venkataraman Balasubramanian
(74) Attorney, Agent, or Firm — Astrazeneca AB

(57) ABSTRACT

The invention concerns a compound of the formula (I)

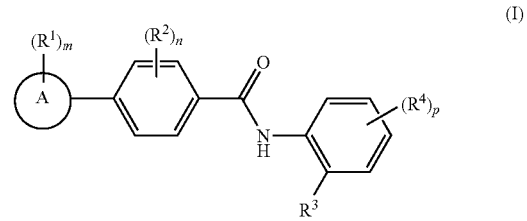

wherein Ring A is heterocyclyl; m is 0-4 and each $R^1$ is a group such as hydroxy, halo, trifluoromethyl and cyano; $R^2$ is halo and n is 0-2; and each $R^4$ is a group such as hydroxy, halo, trifluoromethyl and cyano; p is 0-4; and $R^3$ is amino or hydroxy;
or pharmaceutically-acceptable salts or in-vivo-hydrolysable ester or amide thereof;
processes for their preparation, pharmaceutical compositions containing them and their use in the treatment of diseases or medical conditions mediated by histone deacetylase.

5 Claims, No Drawings

OTHER PUBLICATIONS

Final rejection from USPTO for U.S. Appl. No. 10/509,941 (corresponds to WO 03/087057 A), Apr. 3, 2008.

Koshio et al. Preparation of phenyldiazepane derivatives or salt thereof having anticoagulant activity. XP-002248767, 2000:765431 CAPLUS.

Wolff Manfred E. "Burger's Medicinal Chemistry, 5ed, Part 1", John Wiley & Sons, 1995, pp. 975-977.

Yamada et al. Preparation of benzothiazole and Benzoxazole derivatives and analogs as liquid crystals. XP-002248768, 1994:522228 CAPLUS.

* cited by examiner

BENZAMIDE DERIVATIVES USEFUL AS HISTONE DEACETYLASE INHIBITORS

This application is a continuation of U.S. application Ser. No. 12/211,510 (filed Sep. 16, 2008), which is a continuation of U.S. application Ser. No. 10/509,941 (filed Oct. 1, 2004), which is a U.S. National Stage under 35 USC 371 of International Application No. PCT/GB03/01442 (filed Apr. 2, 2003), which claims priority under 35 U.S.C. §119 (a)-(d) to United Kingdom Application No. 0207863.2 (filed Apr. 5, 2002) and to United Kingdom Application No. 0229930.3 (filed Dec. 21, 2002).

This invention relates to benzamide derivatives, or pharmaceutically acceptable salts or in vivo hydrolysable esters or amides thereof. These benzamide derivatives possess histone deacetylase (HDAC) inhibitory activity and accordingly have value in the treatment of disease states associated with cancer (Marks et al., Nature Reviews, 1, 194-202, (2001)), cystic fibrosis (Li, S. et al, J. Biol. Chem., 274, 7803-7815, (1999)), Huntingdons chorea (Steffan, J. S. et al., Nature, 413, 739-743, (2001)) and sickle cell anaemia (Gabbianelli, M. et al., Blood, 95, 3555-3561, (2000)), and accordingly are useful in methods of treatment of a warm-blooded animal, such as man. The invention also relates to processes for the manufacture of said benzamide derivatives, to pharmaceutical compositions containing them and to their use in the manufacture of medicaments to inhibit HDAC in a warm-blooded animal, such as man.

In the eukaryotic cell, DNA is compacted to prevent transcription factor accessibility. When the cell is activated this compact DNA is made available to DNA-binding proteins, thereby allowing the induction of gene transcription (Beato, M., J. Med. Chem., 74, 711-724 (1996); Wolffe, A. P., Nature, 387, 16-17 (1997)). Nuclear DNA associates with histones to form a complex known as chromatin. The core histones, termed H2A, H2B, H3 and H4 surrounded by 146 base pairs of DNA form the fundamental unit of chromatin, the nucleosome. The N-terminal tails of the core histones contain lysines that are sites for post-transcriptional acetylation. Acetylation neutralizes the potential of the side chain to form a positive charge on the lysine side chain, and is thought to impact chromatin structure.

Histone Deacetylases (HDACs) are zinc-containing enzymes which catalyse the removal of acetyl groups from the ε-amino termini of lysine residues clustered near the amino terminus of nucleosomal histones. HDACs may be divided into two classes, the first (HDAC 1, 2, 3 and 8) represented by yeast Rpd3-like proteins, and the second (HDAC 4, 5, 6, 7, 9 and 10) represented by yeast Hdal-like proteins. The reversible process of acetylation is important in transcriptional regulation and cell-cycle progression. HDAC deregulation has been associated with several cancers and HDAC inhibitors, such as Trichostatin A (a natural product isolated from Streptomyces hygroscopicus), have been shown to exhibit significant anti-tumour effects and inhibition of cell-growth (Meinke, P. T., Current Medicinal Chemistry, 8, 211-235 (2001)). Yoshida et al, Exper. Cell Res., 177, 122-131 (1988) teaches that Trichostatin A causes arrest of rat fibroblasts at the G1 and G2 phases of the cell cycle, thereby implicating HDAC in cell cycle regulation. Furthermore, Trichostatin A has been shown to induce terminal differentiation, inhibit cell growth, and prevent the formation of tumours in mice (Finnin et al., Nature, 401, 188-193 (1999)).

To date only a few inhibitors of HDAC are known in the art. There is thus a need to identify additional HDAC inhibitors.

Accordingly, the present invention provides a compound of the formula (I):

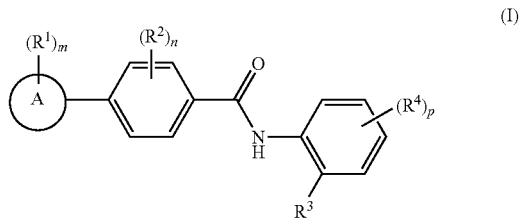

wherein:
Ring A is a heterocyclyl, wherein if said heterocyclyl contains an —NH— moiety that nitrogen may be optionally substituted by a group selected from K;

$R^1$ is a substituent on carbon and is selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$ amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$ sulphamoyl, aryl, aryloxy, aryl$C_{1-6}$alkyl, heterocyclic group, (heterocyclic group)$C_{1-6}$alkyl, or a group (B-E-); wherein $R^1$, including group (B-E-), may be optionally substituted on carbon by one or more W; and wherein if said heterocyclic group contains an —NH— moiety that nitrogen may be optionally substituted by J;

W is halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$ amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, or a group (B'-E'-); wherein W, including group (B'-E'-), may be optionally substituted on carbon by one or more Y;

Y and Z are independently selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$ carbamoyl, $C_{1-6}$alkylS(O)$_a$ wherein a is 0 to 2, $C_{1-6}$alkoxycarbonyl, N—($C_{1-6}$alkyl)sulphamoyl or N,N—($C_{1-6}$alkyl)$_2$ sulphamoyl;

G, J and K are independently selected from $C_{1-8}$alkyl, $C_{2-8}$alkenyl, $C_{1-8}$alkanoyl, $C_{1-8}$alkylsulphonyl, $C_{1-8}$alkoxycarbonyl, carbamoyl, N—($C_{1-8}$alkyl)carbamoyl, N,N—($C_{1-8}$alkyl)carbamoyl, benzyloxycarbonyl, benzoyl, phenylsulphonyl, aryl, aryl$C_{1-6}$alkyl or (heterocyclic group)$C_{1-6}$alkyl; wherein G, J and K may be optionally substituted on carbon by one or more Q; and wherein if said heterocyclic group contains an —NH— moiety that nitrogen may be optionally substituted by hydrogen or $C_{1-6}$alkyl;

Q is halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$ sulphamoyl, aryl, aryloxy, aryl $C_{1-6}$alkyl, aryl$C_{1-6}$alkoxy, heterocyclic group, (heterocyclic group)$C_{1-6}$alkyl, (heterocyclic group)$C_{1-6}$alkoxy, or a group (B"-E"-); wherein Q, including group (B"-E"-), may be optionally substituted on carbon by one or more Z;

B, B' and B" are independently selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, aryl, aryl$C_{1-6}$alkyl, heterocyclic group, (heterocyclic group)$C_{1-6}$alkyl, phenyl or phenyl$C_{1-6}$alkyl; wherein B, B' and B" may be optionally substituted on carbon by one or more D; and wherein if said heterocyclic group contains an —NH— moiety that nitrogen may be optionally substituted by a group selected from G;

E, E' and E" are independently selected from —N($R^a$)—, —O—, —C(O)O—, —OC(O)—, —C(O)—, —N($R^a$)C(O)—, —N($R^a$)C(O)N($R^b$)—, —N($R^a$)C(O)O—, —OC(O)N($R^a$)—, —C(O)N($R^a$)—, —S(O)$_r$—, —SO$_2$N($R^a$)—, —N($R^a$)SO$_2$—; wherein $R^a$ and $R^b$ are independently selected from hydrogen or $C_{1-6}$alkyl optionally substituted by one or more F and r is 0-2;

D and F are independently selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl or N,N—($C_{1-6}$alkyl)$_2$sulphamoyl;

m is 0, 1, 2, 3 or 4; wherein the values of $R^1$ may be the same or different;

$R^2$ is halo;

n is 0, 1 or 2; wherein the values of $R^2$ may be the same or different;

$R^3$ is amino or hydroxy;

$R^4$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, $C_{1-3}$alkanoyloxy, N—($C_{1-3}$alkyl)amino, N,N—($C_{1-3}$alkyl)$_2$amino, $C_{1-3}$alkanoylamino, N—($C_{1-3}$alkyl)carbamoyl, N,N—($C_{1-3}$alkyl)$_2$carbamoyl, $C_{1-3}$alkylS(O)$_a$ wherein a is 0 to 2, $C_{1-3}$alkoxycarbonyl, N—($C_{1-3}$alkyl)sulphamoyl, N,N—($C_{1-3}$alkyl)$_2$sulphamoyl;

p is 0, 1 or 2; wherein the values of $R^4$ may be the same or different;

or a pharmaceutically acceptable salt or in vivo hydrolysable ester or amide thereof; with the proviso that said compound is not
N-(2-amino-6-hydroxyphenyl)-4-(1-methylhomopiperazin-4-yl)benzamide;
N-(2-amino-6-methylphenyl)-4-(1-methylhomopiperazin-4-yl)benzamide;
N-(2-aminophenyl)-4-(1-t-butoxycarbonylhomopiperazin-4-yl)benzamide; or
N-(2-aminophenyl)-4-(1-methylhomopiperazin-4-yl)benzamide.

According to a further aspect of the present invention, there is provided a compound of the formula (I) wherein:

Ring A is a heterocyclyl;

$R^1$ is halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl or a group (B-E-); wherein, B is selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, heterocyclyl, phenyl$C_{1-6}$alkyl or heterocyclyl$C_{1-6}$alkyl; wherein B may be optionally substituted on carbon by one or more D; and wherein if said heterocyclyl contains an —NH— moiety that nitrogen may be optionally substituted by a group selected from G;

E is —N($R^a$)—, —O—, —C(O)O—, —OC(O)—, —C(O)—, —N($R^a$)C(O)—, —C(O)N($R^a$)—, —S(O)$_r$—, —SO$_2$N($R^a$)—, —N($R^a$)SO$_2$—; wherein $R^a$ is hydrogen or $C_{1-6}$alkyl optionally substituted by one or more D and r is 0-2;

D is independently selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

G is selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

m is 0, 1, 2, 3 or 4; wherein the values of $R^1$ may be the same or different;

$R^2$ is halo;

n is 0, 1 or 2; wherein the values of $R^2$ may be the same or different;

$R^3$ is amino or hydroxy;

$R^4$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy $C_{1-3}$alkanoyl, $C_{1-3}$alkanoyloxy, N—($C_{1-3}$alkyl)amino, N,N—($C_{1-3}$ alkyl)$_2$amino, $C_{1-3}$alkanoylamino, N—($C_{1-3}$alkyl)carbamoyl, N,N—($C_{1-3}$alkyl)$_2$carbamoyl, $C_{1-3}$alkylS(O)$_a$ wherein a is 0 to 2, $C_{1-3}$alkoxycarbonyl, N—($C_{1-3}$alkyl)sulphamoyl, N,N—($C_{1-3}$alkyl)$_2$sulphamoyl;

p is 0, 1 or 2; wherein the values of $R^4$ may be the same or different;

or a pharmaceutically acceptable salt or in vivo hydrolysable ester or amide thereof; with the proviso that said compound is not N-(2amino-6-hydroxyphenyl)-4-(1-methylhomopiperazin-4-yl)benzamide; N-(2amino-6-methylphenyl)-4-(1-methylhomopiperazin-4-yl) lbenzamide; N-(2-aminophenyl)-4-(1-t-butoxycarbonylhomopiperazin-4-yl)lbenzamide; or N-(2-aminophenyl)-4-(1-methylhomopiperazin-4-yl)lbenzamide.

In this specification the term "alkyl" includes both straight and branched chain alkyl groups. For example, "$C_{1-8}$alkyl" and "$C_{1-6}$alkyl" includes methyl, ethyl, propyl, isopropyl, pentyl, hexyl, heptyl, and t-butyl. However, references to individual alkyl groups such as 'propyl' are specific for the straight-chained version only and references to individual branched chain alkyl groups such as 'isopropyl' are specific for the branched chain version only. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a ring sulphur atom may be optionally oxidised to form the S-oxide(s). Preferably a "heterocyclyl" is a saturated, partially saturated or unsaturated, monocyclic ring containing 5 or 6 atoms of which at least one atom is chosen from nitrogen, sulphur or oxygen or a 8-10 membered bicyclic ring which may, unless otherwise specified, be carbon or nitrogen linked, wherein a ring sulphur atom may be optionally oxidised to form S-oxide(s). Examples and suitable values of the term "heterocyclyl" are thiazolidinyl, pyrrolidinyl, 1,3-benzodioxolyl, 1,2,4-oxadiazolyl, 2-azabicyclo[2.2.1]heptyl, morpholinyl, tetrahydrofuranyl, furanyl, tetrahydropyranyl, piperidinyl, piperazinyl, thiomorpholinyl, 1,3-dioxolanyl, homopiperazinyl, thienyl, pyrrolyl, pyrazolyl, oxadiazolyl, tetrazolyl, oxazolyl, thienopyrimidinyl, thienopyridinyl, thieno[3,2-d]pyrimidinyl, 1,3,5-triazinyl, purinyl, 1,2,3,4-tetrahydroquinolinyl, benzimidazolyl, benzthiazolyl, benzoxazolyl, benzothienyl, benzofuranyl, indazolyl, quinazolinyl, cinnolinyl, phthalazinyl, quinoxalinyl, napthyridinyl, benzotriazolyl, pyrrolothienyl, imidazothienyl, isoxazolyl, imidazolyl, thiadiazolyl, isothiazolyl, 1,2,3-triazolyl, 1,2,4-triazolyl, pyranyl, indolyl, pyrimidyl, thiazolyl, pyrazinyl, pyridazinyl, pyridyl, quinolyl, quinazolinyl, and 1-isoquinolinyl.

A "heterocyclic group" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a $CH_2$ group can optionally be replaced by a C(O), and wherein a ring sulphur atom may be optionally oxidised to form the S-oxide(s). Preferably a "heterocyclic group" is a saturated, partially saturated or unsaturated, monocyclic ring containing 5 or 6 atoms of which at least one atom is chosen from nitrogen, sulphur or oxygen or a 9 or 10 membered bicyclic ring which may, unless otherwise specified, be carbon or nitrogen linked, wherein a $CH_2$ group can optionally be replaced by a C(O), and wherein a ring sulphur atom may be optionally oxidised to form S-oxide(s). Examples and suitable values of the term "heterocyclic group" are pyrrolidinyl, 2-pyrrolidonyl 2,5-dioxopyrrolidinyl, 2,4-dioxoimidazolidinyl, 2-oxo-1,3,4-triazolinyl, oxazolidinyl, 2-oxazolidonyl, 5,6-dihydro-uracilyl, 1,3-benzodioxolyl, 1,2,4-oxadiazolyl, 2-azabicyclo[2.2.1]heptyl, morpholinyl, 2-oxotetrahydrofuranyl, tetrahydrofuranyl, furanyl, tetrahydropyranyl, piperidinyl, piperazinyl, thiomorpholinyl, 1,1-dioxothiomorpholinyl, 1,3-dioxolanyl, homopiperazinyl, thiophenyl, thienopyridinyl, thienopyrimidinyl, thieno[3,2-d]pyrimidinyl, 1,3,5-triazinyl, purinyl, quinolinyl, isoquinolinyl, 1,2,3,4-tetrahydroquinolinyl, tetrahydroisoquinolinyl, imidazolyl, benzimidazolyl, benzothiazolyl, benzoxazolyl, benzothiophenyl, benzofuranyl, indazolyl, quinazolinyl, cinnolinyl, phthalazinyl, quinoxalinyl, napthyridinyl, oxazolyl, isoxazolyl, pyrrolyl, tetrazolyl, thiadiazolyl, isothiazolyl, 1,2,3-triazolyl, 1,2,4-triazolyl, pyranyl, indolyl, isoindolyl, pyrimidinyl, thiazolyl, pyrazolyl, 3-pyrrolinyl, pyrazinyl, pyridazinyl, pyridinyl, pyridonyl, pyrimidonyl and 1-isoquinolinyl.

An "aryl" group is, for example, phenyl, indenyl, indanyl, naphthyl, tetrahydronaphthyl or fluorenyl, preferably phenyl.

An example of "$C_{1-8}$alkanoyloxy" is acetoxy. Examples of "$C_{1-8}$alkoxycarbonyl", "$C_{1-6}$alkoxycarbonyl" and $C_{1-4}$alkoxycarbonyl include methoxycarbonyl, ethoxycarbonyl, n- and t-butoxycarbonyl. Examples of $C_{2-6}$alkynyl are ethynyl and 2-propynyl. Examples of "$C_{1-6}$alkoxy" include methoxy, ethoxy and propoxy. Examples of "$C_{1-6}$alkanoylamino" and $C_{1-3}$alkanoylamino include formamido, acetamido and propionylamino. Examples of "$C_{1-6}$alkylS(O)$_a$ wherein a is 0 to 2" include $C_{1-4}$alkylsulphonyl, $C_{1-3}$alkylS(O)$_a$, methylthio, ethylthio, methylsulphinyl, ethylsulphinyl, mesyl and ethylsulphonyl. Examples of "$C_{1-8}$alkanoyl", "$C_{1-6}$ alkanoyl" and $C_{1-4}$ alkanoyl include $C_{1-3}$alkanoyl, propionyl and acetyl. Examples of "N—$C_{1-6}$alkylamino" and N—($C_{1-3}$alkyl)amino include methylamino and ethylamino. Examples of "N,N—($C_{1-6}$alkyl)$_2$amino" and N,N—($C_{1-2}$alkyl)$_2$amino include di-N-methylamino, di-(N-ethyl)amino, di-(N-butyl)amino and N-ethyl-N-methylamino. Examples of "$C_{2-8}$alkenyl" are $C_{2-6}$alkenyl and $C_{2-3}$alkenyl, and include vinyl, allyl, and 1-propenyl. Examples of "N—($C_{1-8}$alkyl) sulphamoyl" and "N—($C_{1-6}$alkyl)sulphamoyl" are N—($C_{1-3}$alkyl)sulphamoyl, N—(methyl)sulphamoyl and N—(ethyl) sulphamoyl. Examples of "N—($C_{1-6}$alkyl)$_2$sulphamoyl" are N,N—($C_{1-3}$alkyl)$_2$sulphamoyl, N,N-(dimethyl)sulphamoyl and N—(methyl)-N—(ethyl)sulphamoyl. Examples of "N—($C_{1-8}$alkyl)carbamoyl" and "N—($C_{1-6}$alkyl)carbamoyl" are N—($C_{1-4}$ alkyl)carbamoyl, N—($C_{1-3}$alkyl)carbamoyl, methylaminocarbonyl, and ethylaminocarbonyl. Examples of "N,N—($C_{1-8}$alkyl)$_2$carbamoyl" and"N,N—($C_{1-6}$alkyl)$_2$carbamoyl" are N,N—($C_{1-4}$ alkyl)carbamoyl, N,N—($C_{1-2}$alkyl)$_2$carbamoyl, dimethylaminocarbonyl and methylethylaminocarbonyl. Examples of "(heterocyclic group)$C_{1-6}$alkyl" include piperidin-1-ylmethyl, piperidin-1-ylethyl, piperidin-1-ylpropyl, pyridylmethyl, 3-morpholinopropyl, 2-morpholinoethyl and 2-pyrimid-2-ylethyl. Examples of "(heterocyclic group)$C_{1-6}$alkoxy" include (heterocyclic group)methoxy, (heterocyclic group)ethoxy and (heterocyclic group)propoxy. Examples of "aryl$C_{1-6}$alkyl" include benzyl, 2-phenylethyl, 2-phenylpropyl and 3-phenylpropyl Examples of "aryloxy" include phenoxy and naphthyloxy. Examples of "$C_{3-8}$cycloalkyl" include cyclopropyl and cyclohexyl. Examples of "$C_{3-8}$cycloalkyl$C_{1-6}$alkyl" include cyclopropylmethyl and 2-cyclohexylpropyl. Examples of "$C_{1-6}$alkoxycarbonylamino" include methoxycarbonylamino and t-butoxycarbonylamino.

Within this specification composite terms are used to describe groups comprising more that one functionality such as aryl$C_{1-6}$alkyl. Such terms are to be interpreted as is understood by a person skilled in the art. For example aryl$C_{1-6}$alkyl comprises $C_{1-6}$alkyl substituted by aryl and such a group includes benzyl, 2-phenylethyl, 2-phenylpropyl and 3-phenylpropyl.

A suitable pharmaceutically acceptable salt of a compound of the invention is, for example, an acid-addition salt of a compound of the invention which is sufficiently basic, for example, an acid-addition salt with, for example, an inorganic or organic acid, for example acetic, hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

The compounds of the formula (I) may be administered in the form of an in vivo hydrolysable ester or in vivo hydrolysable amide of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I) containing a carboxy group is, for example, a N—$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess HDAC inhibitory activity.

The invention relates to any and all tautomeric forms of the compounds of the formula (I) that possess HDAC inhibitory activity.

Further values of Ring A, $R^1$, $R^2$, $R^3$, $R^4$, m, n and p are as follows. Such values may be used where appropriate with any of the definitions, claims or embodiments defined hereinbefore or hereinafter.

Ring A is a pyridyl, quinolyl, indolyl, pyrimidinyl, morpholinyl, piperidinyl, piperazinyl, pyradazinyl, pyrazinyl, thiazolyl, thienyl, thienopyrimidinyl, thienopyridinyl, purinyl, triazinyl, oxazolyl, pyrazolyl, or furanyl; wherein if Ring A contains an —NH— moiety that nitrogen may be optionally substituted by a group selected from K.

Ring A is pyridin-4-yl, pyridin-3-yl, pyridin-2-yl, quinolin-8-yl, pyrimidin-6-yl, pyrimidin-5-yl, pyrimidin-4-yl, morpholin-4-yl, piperidin-4-yl, piperidin-3-yl, piperidin-2-yl, piperazin-4-yl, pyridazin-5-yl, pyrazin-6-yl, thiazol-2-yl, thien-2-yl, thieno[3,2-d]pyrimidinyl, thieno[3,2b]pyrimidinyl, thieno[3,2b]pyridinyl, purin-6-yl or triazin-6-yl; wherein if Ring A contains an —NH— moiety that nitrogen may be optionally substituted by a group selected from K.

Ring A is a pyridyl, quinolyl, pyrimidyl, morpholinyl, piperidinyl, piperazinyl, pyradazinyl, pyrazinyl, thiazyl or furanyl.

Ring A is a pyridin-4-yl, pyridin-3-yl, pyridin-2-yl, quinoline-8-yl, pyradizin-2-yl, furan-3-yl, morpholinyl, thiazol-2-yl, pyrimidin-6-yl, piperidin-4-yl or piperazin-4-yl.

Ring A is pyridin-4-yl, pyridin-3-yl, quinoline-8-yl, piperidin-4-yl or piperazin-4-yl.

$R^1$ is a substituent on carbon and is selected from halo, amino, $C_{1-6}$alkyl, $C_{1-6}$alkoxy, N—($C_{1-6}$alkyl)amino, aryl, aryloxy, aryl$C_{1-6}$alkyl, heterocyclic group, (heterocyclic group)$C_{1-6}$alkyl, or a group (B-E-); wherein $R^1$, including group (B-E-), may be optionally substituted on carbon by one or more W; and wherein if said heterocyclic group contains an —NH— moiety that nitrogen may be optionally substituted by J;

W is hydroxy, mercapto, $C_{1-6}$alkyl, $C_{1-6}$alkoxy, N,N—($C_{1-6}$ alkyl)$_2$amino or a group (B'-E'-); wherein W, including group (B'-E'-), may be optionally substituted on carbon by one or more Y;

Y and Z are independently selected from halo, nitro, cyano, hydroxy, $C_{1-6}$alkoxy, N,N—($C_{1-6}$alkyl)$_2$amino or $C_{1-6}$alkanoylamino;

G, J and K are independently selected from $C_{1-8}$alkyl, $C_{2-8}$alkenyl, $C_{1-8}$alkanoyl, aryl, aryl$C_{1-6}$alkyl or (heterocyclic group)$C_{1-6}$alkyl; wherein G, J and K may be optionally substituted on carbon by one or more Q; and wherein if said heterocyclic group contains an —NH— moiety that nitrogen may be optionally substituted by hydrogen or $C_{1-6}$alkyl;

Q is cyano, hydroxy, $C_{1-6}$alkoxy, $C_{1-6}$alkanoyloxy, $C_{1-6}$alkoxycarbonyl, $C_{1-6}$alkoxycarbonylamino, aryl, aryloxy or a group (B"-E"-); wherein Q, including group (B"-E"-), may be optionally substituted on carbon by one or more Z;

B, B' and B" are independently selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, aryl, aryl$C_{1-6}$alkyl, heterocyclic group, (heterocyclic group)$C_{1-6}$alkyl, phenyl or phenyl$C_{1-6}$alkyl; wherein B, B' and B" may be optionally substituted on carbon by one or more D; and wherein if said heterocyclic group contains an —NH— moiety that nitrogen may be optionally substituted by a group selected from G;

E, E' and E" are independently selected from —N($R^a$)—, —O—, —C(O)O—, —OC(O)—, —C(O)—, —N($R^a$)C(O)—, —N($R^a$)C(O)N($R^b$)—, —N($R^a$)C(O)O—, —OC(O)N($R^a$)—, —C(O)N($R^a$)—, —S(O)$_r$—, —SO$_2$N($R^a$)—, —N($R^a$)SO$_2$—; wherein $R^a$ and $R^b$ are independently selected from hydrogen or $C_{1-6}$alkyl optionally substituted by one or more F and r is 0-2;

D and F are independently selected from halo, $C_{1-6}$alkoxy or N,N—($C_{1-6}$alkyl)$_2$amino.

$R^1$ is a substituent on carbon and is selected from fluoro, chloro, amino, methyl, ethyl, propyl, methoxy, N-methylamino, N-ethylamino, N-propylamino, N-butylamino, phenyl, naphthylethyl, piperizin-1-yl, piperidin-1-yl, piperidin-4-yl, 2-(thiomethyl)-pyrimidin-4-yl, tetrahydrofuran-2-ylmethyl, tetrahydropyran-2-ylmethyl, 1,2,5-thiadiazol-3-ylmethyl, piperidin-1-ylmethyl, pyridin-2-ylmethyl, or a group (B-E-); wherein R', including group (B-E-), may be optionally substituted on carbon by one or more W; and wherein if said heterocyclic group contains an —NH— moiety that nitrogen may be optionally substituted by J;

W is hydroxy, methyl, ethyl, ethoxy, N,N-(diethyl)amino, N,N-(dibutyl)amino, or a group (B'-E'-); wherein W, including group (B'-E'-), may be optionally substituted on carbon by one or more Y;

Y and Z are independently selected from fluoro, chloro, bromo, nitro, cyano hydroxy, methoxy, N,N-(dimethyl)amino or methylcarbonylamino;

G, J and K are independently selected from methyl, ethyl, propyl, pentyl, 2-methylbutyl, butyl, acetyl, benzyl, 3-(pyrrol-1-yl)propyl or pyrrolidin-2-one-(5S)-methyl; wherein G, J and K may be optionally substituted on carbon by one or more Q; and wherein if said heterocyclic group contains an —NH— moiety that nitrogen may be optionally substituted by hydrogen or methyl;

Q is cyano, hydroxy, methoxy, ethoxy, methylcarbonyloxy, methoxycarbonyl, t-butoxycarbonlyamino, phenyl or a group (B''-E''-); wherein Q, including group (B''-E''-), may be optionally substituted on carbon by one or more Z;

B, B' and B'' are independently selected from methyl, ethyl, propyl, cyclohexyl, phenyl, benzyl, 1,2,3,4-tetrahydroquinolinyl, 3-morpholinopropyl, 2-morpholinoethyl, 2-pyrrolidin-1-ylethyl, 3-morpholinopropyl, 3-(4-methylpiperazin-1-yl)propyl, 2-piperidin-1-ylethyl, 3-piperidin-1-ylpropyl, pyridin-3-ylmethyl or imidazol-1-ylpropyl; wherein B, B' and B'' may be optionally substituted on carbon by one or more D; and wherein if said heterocyclic group contains an —NH— moiety that nitrogen may be optionally substituted by a group selected from G;

E, E' and E'' are independently selected from —N($R^a$)—, —O—, —C(O)—, —NHC(O)—, —N($R^a$)C(O)O—; wherein $R^a$ is hydrogen or methyl optionally substituted by one or more F;

D and F are independently selected from fluoro, methoxy or ethoxy.

$R^1$ is fluoro, chloro, amino, methyl, methoxy, 3-morpholin-4-ylpropylamino, (3-morpholin-4-yl)ethylamino, acetyl, benzyl, methoxycarbonylmethyl, 2-pyrrolidin-1-ylethoxy, 3-morpholinopropoxy, N-(2-fluorophenyl)propanamide, 4-(diethylamino)phenylcarbonylmethyl, 3-(4-methylpiperazin-1-yl)propylamino, 2-piperidin-1-ylethylamino, 2-[N,N-(diethyl)amino]ethylamino, pyridin-3-ylmethylamino, 3-piperidin-1-ylpropylamino, imidazol-1-ylpropylamino, 3-methoxypropylamino, 3-morpholinopropylamino, piperazin-1-yl, N-ethylamino, 4-methylpiperazin-1-yl, 1-(3-phenoxy)propyl, 1-(3-cyanophenyl)methyl, 1-(4-cyanophenyl)methyl, tetrahydrofuran-2-ylmethyl, 1-(3-benzyloxy)propyl, 3-methoxybenzyl, 2,3-dihydroxypropyl, 2-(methylcarbonyloxy)ethyl, 3-(pyrrol-1-yl)propyl, 1-[3-(2-methoxyethoxy)]propyl, 2-(4-acetamidophenyoxy)ethyl, 2-(t-butoxycarbonylamino)ethyl, 2-(t-butoxycarbonylamino)propyl, 2-[(2-methoxyphenyl)oxy]ethyl, (1,2,3,4-tetrahydroquinolin-1-yl)acetyl, 2-[N-(2-fluorophenyl)ylacetamide]ethyl, methoxycarbonylmethyl, 2-(ethoxy)ethyl, 4-methylpent-3-enyl, tetrahydropyran-2-ylmethyl, 1-(2S)-2-methylbutyl, 4-(benzyloxy)butyl, 2-[4-(nitro)phenoxy)]ethyl, 2-[N,N-(dibutyl)amino]ethylamino, 3-[(N-methyl-N-phenyl)amino]propylamino, N-3-[2-(dimethylamino)ethoxy]propylamino, 2-[4-(acetamido)phenoxy]ethyl, 2-[4-(hydroxyphenoxy)]ethyl, 1,2,5-thiadiazol-3-ylethyl, piperidin-1-ylmethyl, 2-[4-(chloro)phenoxy]ethyl, pyrrolidin-2-one-(5S)-methyl, phenylaminocarbonyloxymethyl, cyclohexylaminocarbonyloxymethyl, 2-(thiomethyl)-pyrimidin-4-yl or pyridin-2-ylmethyl.

$R^1$ is halo, amino, $C_{1-6}$alkyl, $C_{1-6}$alkoxy, $C_{1-3}$alkanoyloxy, N—($C_{1-3}$alkyl)amino, N,N—($C_{1-3}$alkyl)$_2$amino, $C_{1-3}$alkanoylamino, N—($C_{1-3}$alkyl)carbamoyl, N,N—($C_{1-3}$alkyl)$_2$carbamoyl.

$R^1$ is halo, amino, $C_{1-6}$alkyl or $C_{1-6}$alkoxy.

$R^1$ is halo, amino, methyl or methoxy.

m is 0, 1, 2, 3 or 4; wherein the values of $R^1$ may be the same or different.

m is 0, 1, or 2; wherein the values of $R^1$ may be the same or different.

m is 0 or 1.

m is 0.

m is 1.

$R^2$ is halo.

$R^2$ is fluoro or chloro.

$R^2$ is fluoro.

n is 0, 1 or 2, wherein the values of $R^2$ may be the same or different.

n is 0 or 1.

n is 0.

n is 1.

$R^3$ is amino or hydroxy.

$R^3$ is amino.

$R^3$ is hydroxy.

$R^4$ is halo, nitro, cyano, hydroxy, trifluoromethyl, trifluoromethoxy, amino, carboxy or carbamoyl.

$R^4$ is halo, cyano, trifluoromethyl or trifluoromethoxy.

$R^4$ is halo.

p is 0, 1 or 2, wherein the values of $R^4$ may be the same or different.

p is 0 or 1.

p is 0.

p is 1.

Therefore in an additional aspect of the invention there is provided a compound of formula (I) (as depicted above) wherein:

Ring A is a pyridyl, quinolyl, indolyl, pyrimidinyl, morpholinyl, piperidinyl, piperazinyl, pyradazinyl, pyrazinyl, thiazolyl, thienyl, thienopyrimidinyl, thienopyridinyl, purinyl, triazinyl, oxazolyl, pyrazolyl, or furanyl; wherein if Ring A contains an —NH— moiety that nitrogen may be optionally substituted by a group selected from K;

$R^1$ is a substituent on carbon and is selected from halo, amino, $C_{1-6}$alkyl, $C_{1-6}$alkoxy, N—($C_{1-6}$alkyl)amino, aryl, aryloxy, aryl$C_{1-6}$alkyl, heterocyclic group, (heterocyclic group)$C_{1-6}$alkyl, or a group (B-E-); wherein $R^1$, including group (B-E-), may be optionally substituted on carbon by one or more W; and wherein if said heterocyclic group contains an —NH— moiety that nitrogen may be optionally substituted by J;

W is hydroxy, mercapto, $C_{1-6}$alkyl, $C_{1-6}$alkoxy, N,N—($C_{1-6}$alkyl)$_2$amino or a group (B'-E'-); wherein W, including group (B'-E'-), may be optionally substituted on carbon by one or more Y;

Y and Z are independently selected from halo, nitro, cyano, hydroxy, $C_{1-6}$alkoxy, N,N—($C_{1-6}$alkyl)$_2$amino or $C_{1-6}$alkanoylamino;

G, J and K are independently selected from $C_{1-8}$alkyl, $C_{2-8}$alkenyl, $C_{1-8}$alkanoyl, aryl, aryl$C_{1-6}$alkyl or (heterocyclic group)$C_{1-6}$alkyl; wherein G, J and K may be optionally substituted on carbon by one or more Q; and wherein if said heterocyclic group contains an —NH— moiety that nitrogen may be optionally substituted by hydrogen or $C_{1-6}$alkyl;

Q is cyano, hydroxy, $C_{1-6}$alkoxy, $C_{1-6}$alkanoyloxy, $C_{1-6}$alkoxycarbonyl, $C_{1-6}$alkoxycarbonylamino, aryl, aryloxy or a group (B''-E''-); wherein Q, including group (B''-E''-), may be optionally substituted on carbon by one or more Z;

B, B' and B'' are independently selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, aryl, aryl$C_{1-6}$alkyl, heterocyclic group, (heterocyclic group)$C_{1-6}$alkyl, phenyl or phenyl$C_{1-6}$alkyl; wherein B, B' and B'' may be optionally substituted on carbon by one or more D; and wherein if said heterocyclic group contains an —NH— moiety that nitrogen may be optionally substituted by a group selected from G;

E, E' and E'' are independently selected from —N($R^a$)—, —O—, —C(O)O—, —OC(O)—, —C(O)—, —N($R^a$)C(O)—, —N($R^a$)C(O)N($R^a$)—, —N($R^a$)C(O)O—, —OC(O)N($R^a$)—, —C(O)N($R^a$)—, —S(O)$_r$—, —SO$_2$N($R^a$)—, —N($R^a$)SO$_2$—; wherein $R^a$ and $R^b$ are independently selected from hydrogen or $C_{1-6}$alkyl optionally substituted by one or more F and r is 0-2;

D and F are independently selected from halo, $C_{1-6}$alkoxy or N,N—($C_{1-6}$alkyl)$_2$amino;

m is 0, 1, 2, 3 or 4; wherein the values of $R^1$ may be the same or different;

$R^2$ is fluoro or chloro;

n is 0, 1 or 2, wherein the values of $R^2$ may be the same or different;

$R^3$ is amino or hydroxy;

$R^4$ is halo, nitro, cyano, hydroxy, trifluoromethyl, trifluoromethoxy, amino, carboxy or carbamoyl;

p is 0, 1 or 2, wherein the values of $R^4$ may be the same or different;

or a pharmaceutically acceptable salt or in vivo hydrolysable ester or amide thereof.

Therefore in an additional aspect of the invention there is provided a compound of formula (I) (as depicted above) wherein:

Ring A is pyridin-4-yl, pyridin-3-yl, pyridin-2-yl, quinolin-8-yl, pyrimidin-6-yl, pyrimidin-5-yl, pyrimidin-4-yl, morpholin-4-yl, piperidin-4-yl, piperidin-3-yl, piperidin-2-yl, piperazin-4-yl, pyridazin-5-yl, pyrazin-6-yl, thiazol-2-yl, thien-2-yl, thieno[3,2-d]pyrimidinyl, thieno[3,2b]pyrimidinyl, thieno[3,2b]pyridinyl, purin-6-yl or triazin-6-yl; wherein if Ring A contains an —NH— moiety that nitrogen may be optionally substituted by a group selected from K;

$R^1$ is a substituent on carbon and is selected from fluoro, chloro, amino, methyl, ethyl, propyl, methoxy, N-methylamino, N-ethylamino, N-propylamino, N-butylamino, phenyl, naphthylethyl, piperazin-1-yl, piperidin-1-yl, piperidin-4-yl, 2-(thiomethyl)-pyrimidin-4-yl, tetrahydrofuran-2-ylmethyl, tetrahydropyran-2-ylmethyl, 1,2,5-thiadiazol-3-ylethyl, piperidin-1-ylmethyl, pyridin-2-ylmethyl, or a group (B-E-); wherein $R^1$, including group (B-E-), may be optionally substituted on carbon by one or more W; and wherein if said heterocyclic group contains an —NH— moiety that nitrogen may be optionally substituted by J;

W is hydroxy, methyl, ethyl, ethoxy, N,N-(diethyl)amino, N,N-(dibutyl)amino, or a group (B'-E'-); wherein W, including group (B'-E'-), may be optionally substituted on carbon by one or more Y;

Y and Z are independently selected from fluoro, chloro, bromo, nitro, cyano, hydroxy, methoxy, N,N-(dimethyl)amino or methylcarbonylamino;

G, J and K are independently selected from methyl, ethyl, propyl, pentyl, 2-methylbutyl, butyl, acetyl, benzyl, 3-(pyrrol-1-yl)propyl or pyrrolidin-2-one-(5S)-methyl; wherein G, J and K may be optionally substituted on carbon by one or more Q; and wherein if said heterocyclic group contains an —NH— moiety that nitrogen may be optionally substituted by hydrogen or methyl;

Q is cyano, hydroxy, methoxy, ethoxy, methylcarbonyloxy, methoxycarbonyl, t-butoxycarbonylamino, phenyl or a group (B"-E"-); wherein Q, including group (B"-E"-), may be optionally substituted on carbon by one or more Z;

B, B' and B" are independently selected from methyl, ethyl, propyl, cyclohexyl, phenyl, benzyl, 1,2,3,4-tetrahydroquinolinyl, 3-morpholinopropyl, 2-morpholinoethyl, 2-pyrrolidin-1-ylethyl, 3-morpholinopropyl, 3-(4-methylpiperazin-1-yl)propyl, 2-piperidin-1-ylethyl, 3-piperidin-1-ylpropyl, pyridin-3-ylmethyl or imidazol-1-ylpropyl; wherein B, B' and B" may be optionally substituted on carbon by one or more D; and wherein if said heterocyclic group contains an —NH— moiety that nitrogen may be optionally substituted by a group selected from G;

E, E' and E" are independently selected from —N($R^a$)—, —O—, —C(O)—, —NHC(O)—, —N($R^a$)C(O)O—; wherein $R^a$ is hydrogen or methyl optionally substituted by one or more F;

D and F are independently selected from fluoro, methoxy or ethoxy;

m is 0, 1, or 2; wherein the values of $R^1$ may be the same or different;

$R^2$ is fluoro;

n is 0 or 1;

$R^3$ is amino;

$R^4$ is halo;

p is 0, 1 or 2, wherein the values of $R^4$ may be the same or different;

or a pharmaceutically acceptable salt or in vivo hydrolysable ester or amide thereof.

In another aspect of the invention, preferred compounds of the invention are any one of the Examples, or a pharmaceutically acceptable salt or an in vivo hydrolysable ester or amide thereof.

In another aspect of the invention there is provided a compound of the formula (I) or a or a pharmaceutically acceptable salt thereof.

Another aspect of the present invention provides a process for preparing a compound of formula (I) or a pharmaceutically acceptable salt or an in vivo hydrolysable ester thereof which process (wherein Ring A, $R^1$, $R^2$, $R^3$, $R^4$, m, n and p are, unless otherwise specified, as defined in formula (I)) comprises of:

(a) The reaction of a compound of the formula (II)

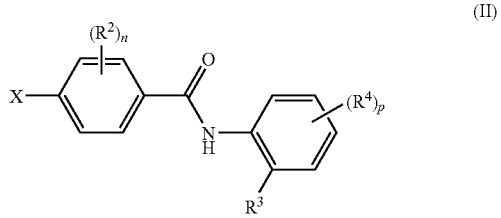

wherein X is a reactive group, with a compound of the formula (III)

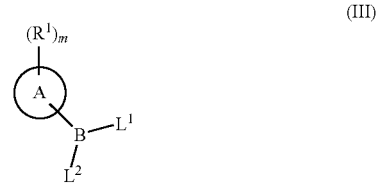

wherein $L^1$ and $L^2$ are ligands;

(b) The reaction of a compound of the formula (IV)

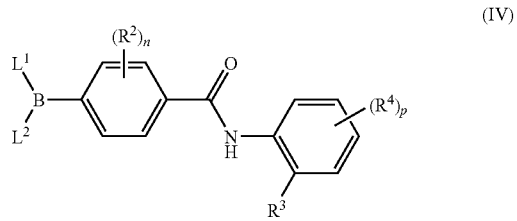

wherein $L^1$ and $L^2$ are ligands, with a compound of the formula (V)

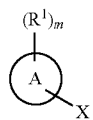

wherein X is a reactive group; or (c) The reaction, in the presence of 4-(4,6-dimethoxy-1,3,5-triazinyl-2-yl)-4-methylmorpholinium chloride, of a compound of the formula (VI)

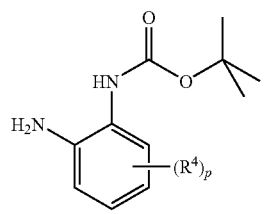

with a compound of the formula (VII)

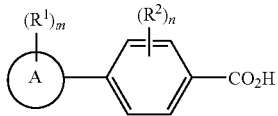

and thereafter if necessary:
i) converting a compound of the formula (I) into another compound of the formula (I); and/or
ii) removing any protecting groups.

A suitable base for process (a), (b) or (c) is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride, or a metal alkoxide such as sodium ethoxide.

A suitable reactive group X is, for example, a halo, alkoxy, aryloxy or sulphonyloxy group, for example a chloro, bromo, methoxy, phenoxy, methanesulphonyloxy, trifluoromethanesulphonyloxy or toluene-4-sulphonyloxy group. The reactions are conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran, 1,2-dimethoxyethane or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reactions are conveniently carried out at a temperature in the range, for example, 10 to 250° C., preferably in the range 40 to 80° C.

A suitable value for the ligands $L^1$ and $L^2$ which are present on the boron atom include, for example, a hydroxy, (1-4C) alkoxy or (1-6C)alkyl ligand, for example a hydroxy, methoxy, ethoxy, propoxy, isopropoxy, butoxy, methyl, ethyl, propyl, isopropyl or butyl ligand. Alternatively the ligands $L^1$ and $L^2$ may be linked such that, together with the boron atom to which they are attached, they form a ring. For example, $L^1$ and $L^2$ together may define an oxy-(2-4C)alkylene-oxy group, for example an oxyethyleneoxy or oxytrimethyleneoxy group such that, together with the boron atom to which they are attached, they form a cyclic boronic acid ester group;

A suitable catalyst for process (a) or (b) includes, for example, a metallic catalyst such as a palladium(0), palladium(II), nickel(0) or nickel(II) catalyst, for example tetrakis(triphenylphosphine)palladium(0), palladium(II) chloride, palladium(II) bromide, bis(triphenylphosphine)palladium (II) chloride, tetrakis(triphenylphosphine)nickel(0), nickel (II) chloride, nickel(II) bromide or bis(triphenylphosphine) nickel(II) chloride. In addition a free radical initiator may conveniently be added, for example an azo compound such as azo(bisisobutyronitrile);

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halo group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Biological Assays

The following assays can be used to measure the effects of the compounds of the present invention as HDAC inhibitors, as inhibitors in vitro of pooled histone deacetylases from nuclear extracts prepared from the human cervical cancer cell line HeLa, as inhibitors in vitro of recombinant human HDAC1 produced in Hi5 insect cells, and as inducers in vitro of Histone H3 acetylation in whole cells.

(a) In Vitro Enzyme Assay of Pooled Histone Deacetylases

HDAC inhibitors were screened against pooled histone deacetylases from nuclear extracts prepared from the human cervical cancer cell line HeLa.

The deacetylase assays were carried out in a 40 µl reaction. 2.5 µg of nuclear extract diluted in 15 µl of reaction buffer (25 mM TrisHCl (pH 8), 137 mM NaCl, 2.7 mM KCl, 1 mM MgCl$_2$) was mixed with either buffer alone (5 µl) or buffer containing compound (5 µl) for 30 minutes at ambient temperature. 25 µM fluor-de-lys substrate (Biomol) diluted in 20 µl of buffer was then added to the reaction and incubated for one hour at ambient temperature. The reaction was stopped by addition of an equal volume (40 µl) fluor de lys developer (Biomol) containing Trichostatin A at 2 µM. The reaction was allowed to develop for 30 minutes at ambient temperature and then fluorescence measured at an excitation wavelength of 360 nM and an emission wavelength of 465 nM. IC$_{50}$ values for HDAC enzyme inhibitors were determined by performing dose response curves with individual compounds and determining the concentration of inhibitor producing fifty percent decrease in the maximal signal (no inhibitor control).

(b) In Vitro Enzyme Assay of recombinant HDAC1

HDAC inhibitors were screened against recombinant human HDAC1 produced in Hi5 insect cells. The enzyme was cloned with a FLAG tag at the C-terminal of the gene and affinity purified using Anti-FLAG M2 agarose from SIGMA (A2220).

The deacetylase assays were carried out in a 50 µl reaction. 75 ng of enzyme diluted in 15 µl of reaction buffer (25 mM TrisHCl (pH 8), 137 mM NaCl, 2.7 mM KCl, 1 mM MgCl$_2$) was mixed with either buffer alone (5 µl) or buffer containing compound (10 µl) for 30 minutes at ambient temperature. 50 µM fluor-de-lys substrate (Biomol) diluted in 25 µl of buffer was then added to the reaction and incubated for one hour at ambient temperature. The reaction was stopped by addition of an equal volume (50 µl) fluor de lys developer (Biomol) containing Trichostatin A at 2 µM. The reaction was allowed to develop for 30 minutes at ambient temperature and then fluorescence measured at an excitation wavelength of 360 nM and an emission wavelength of 465 nM. IC$_{50}$ values for HDAC enzyme inhibitors were determined by performing dose response curves with individual compounds and determining the concentration of inhibitor producing fifty percent decrease in the maximal signal (no inhibitor control).

(c) In Vitro Enzyme Assay of Histone Deacetylase Activity in Whole Cells

Histone H3 acetylation in whole cells using immunohistochemistry and analysis using the Cellomics arrayscan. A549 cells were seeded in 96 well plates at $1 \times 10^4$ cells/well, and allowed to adhere overnight. They were treated with inhibitors for 24 hours and then fixed in 1.8% formaldehyde in tris buffered saline (TBS) for one hour. Cells were permeabilized with ice-cold methanol for 5 minutes, rinsed in TBS and then blocked in TBS 3% low-fat dried milk for 90 minutes. Cells were then incubated with polyclonal antibodies specific for the acetylated histone H3 (Upstate #06-599) diluted 1 in 500 in TBS 3% milk for one hour. Cells were rinsed three times in TBS and then incubated with fluorescein conjugated secondary antibodies (Molecular Probes #A11008) & Hoechst 333542 (1 µg/ml) (Molecular Probes #H3570) in TBS 1% Bovine serum albumin (Sigma #B6917) for one hour. Unbound antibody was removed by three rinses with TBS and after the final rinse 100 µl of TBS was added to the cells and the plates sealed and analysed using the Cellomics arrayscan.

EC$_{50}$ values for HDAC inhibitors were determined by performing dose response curves with individual compounds and then determining the concentration of inhibitor producing fifty percent of the maximal signal (reference compound control—Trichostatin A (Sigma)).

Although the pharmacological properties of the compounds of the formula (I) vary with structural change as expected, in general activity possessed by compounds of the Formula I, may be demonstrated at the following concentrations or doses in one or more of the above tests (a) and (b):—

Test (a):—IC$_{50}$ in the range, for example, <50.0 µM;
Test (b):—IC$_{50}$ in the range, for example, <2.5 µM;
Test (c):—EC$_{50}$ in the range, for example, <9.0 µM;

According to a further aspect of the invention there is provided a pharmaceutical composition which comprises a compound of the formula (I), or a pharmaceutically acceptable salt or in vivo hydrolysable ester or amide thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

We have found that the compounds defined in the present invention, or a pharmaceutically acceptable salt or in vivo hydrolysable ester or amide thereof, are effective cell cycle inhibitors (anti-cell proliferation agents), which property is believed to arise from their HDAC inhibitory properties. We also believe that the compounds of the present invention may be involved in the inhibition of angiogenesis, activation of apoptosis and differentiation. Accordingly the compounds of the present invention are expected to be useful in the treatment of diseases or medical conditions mediated alone or in part by HDAC enzymes, i.e. the compounds may be used to produce a HDAC inhibitory effect in a warm-blooded animal in need of such treatment. Thus the compounds of the present invention provide a method for treating the proliferation of malignant cells characterised by inhibition of HDAC enzymes, i.e. the compounds may be used to produce an anti-proliferative effect mediated alone or in part by the inhibition of HDACs.

According to one aspect of the present invention there is provided a compound of the formula (I), or a pharmaceutically acceptable salt or in vivo hydrolysable ester or amide thereof, as defined hereinbefore for use in a method of treatment of the human or animal body by therapy.

Thus according to a further aspect of the invention there is provided a compound of the formula (I), or a pharmaceutically acceptable salt or in vivo hydrolysable ester or amide thereof, as defined hereinbefore for use as a medicament.

According to a further aspect of the invention there is provided the use of a compound of the formula (I), or a pharmaceutically acceptable salt or in vivo hydrolysable ester or amide thereof, as defined hereinbefore in the manufacture of a medicament for use in the production of a HDAC inhibitory effect in a warm-blooded animal such as man.

According to a further feature of this aspect of the invention there is provided a method for producing a HDAC inhibitory effect in a warm-blooded animal, such as man, in need of such treatment which comprises administering to said animal an effective amount of a compound of the formula (I), or a pharmaceutically acceptable salt or in vivo hydrolysable ester or amide thereof, as defined hereinbefore.

According to a further aspect of the invention there is provided the use of a compound of the formula (I), or a pharmaceutically acceptable salt or in vivo hydrolysable ester or amide thereof, as defined hereinbefore in the manufacture of a medicament for use in the production of a cell cycle inhibitory (anti-cell-proliferation) effect in a warm-blooded animal such as man.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of the formula (I), or a pharmaceutically acceptable salt or in vivo hydrolysable ester or amide thereof, as defined hereinbefore.

According to an additional feature of this aspect of the invention there is provided a method of treating cancer in a warm-blooded animal, such as man, in need of such treatment which comprises administering to said animal an effective amount of a compound of the formula (I), or a pharmaceutically acceptable salt or in vivo hydrolysable ester or amide thereof, as defined hereinbefore.

According to a further feature of the invention there is 74a compound of the formula (I), or a pharmaceutically acceptable salt or in vivo hydrolysable ester or amide thereof, as defined hereinbefore in the manufacture of a medicament for use in the treatment of cancer.

According to an additional feature of this aspect of the invention there is provided a compound of the formula (I), or a pharmaceutically acceptable salt or in vivo hydrolysable ester or amide thereof, as defined hereinbefore, for use in the treatment of cancer.

In a further aspect of the present invention there is provided the use of a compound of the formula (I), or a pharmaceutically acceptable salt or in vivo hydrolysable ester or amide thereof, as defined hereinbefore, in the manufacture of a medicament for use in lung cancer, colorectal cancer, breast cancer, prostate cancer, lymphoma and leukaemia.

In a further aspect of the present invention the is provided a method of treating lung cancer, colorectal cancer, breast cancer, prostate cancer, lymphoma or leukaemia, in a warm-blooded animal, such as man, in need of such treatment which comprises administering to said animal an effective amount of a compound of the formula (I), or a pharmaceutically acceptable salt or in vivo hydrolysable ester or amide thereof, as defined hereinbefore.

Cancers that are amenable to treatment with the present invention include oesophageal cancer, myeloma, hepatocellular, pancreatic and cervical cancer, Ewings tumour, neuroblastoma, kaposis sarcoma, ovarian cancer, breast cancer, colorectal cancer, prostate cancer, bladder cancer, melanoma, lung cancer [including non small cell lung cancer (NSCLC) and small cell lung cancer (SCLC)], gastric cancer, head and neck cancer, brain cancer, renal cancer, lymphoma and leukaemia.

There is further provided is a compound of the formula (I), or a pharmaceutically acceptable salt or in vivo hydrolysable ester or amide thereof, as defined hereinbefore, for use in a method of treating inflammatory diseases, autoimmune diseases and allergic/atopic diseases.

In particular a compound of the formula (I), or a pharmaceutically acceptable salt or in vivo hydrolysable ester or amide thereof, as defined hereinbefore, is provided for use in a method of treating inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis), multiple sclerosis, atherosclerosis, spondyloarthropathies (ankylosing spondylitis, psoriatic arthritis, arthritis connected to ulcerative colitis), AIDS-related neuropathies, systemic lupus erythematosus, asthma, chronic obstructive lung diseases, bronchitis, pleuritis, adult respiratory distress syndrome, sepsis, and acute and chronic hepatitis (either viral, bacterial or toxic).

Further provided is a compound of the formula (I), or a pharmaceutically acceptable salt or in vivo hydrolysable ester or amide thereof, as defined hereinbefore, for use as a medicament in the treatment of inflammatory diseases, autoimmune diseases and allergic/atopic diseases in a warm-blooded animal such as man.

In particular a compound of the formula (I), or a pharmaceutically acceptable salt or in vivo hydrolysable ester or amide thereof, as defined hereinbefore, is provided for use as a medicament in the treatment of inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis), multiple sclerosis, atherosclerosis, spondyloarthropathies (ankylosing spondylitis, psoriatic arthritis, arthritis connected to ulcerative colitis), AIDS-related neuropathies, systemic lupus erythematosus, asthma, chronic obstructive lung diseases, bronchitis, pleuritis, adult respiratory distress syndrome, sepsis, and acute and chronic hepatitis (either viral, bacterial or toxic).

Further provided is the use of a compound of the formula (I), or a pharmaceutically acceptable salt or in vivo hydrolysable ester or amide thereof, as defined hereinbefore, in the manufacture of a medicament for use in the treatment of inflammatory diseases, autoimmune diseases and allergic/atopic diseases in a warm-blooded animal such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The HDAC inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may include one or more of the following categories of anti-tumour agents:

(i) other cell cycle inhibitory agents that work by the same or different mechanisms from those defined hereinbefore, for example cyclin dependent kinase (CDK) inhibitors, in particular CDK2 inhibitors;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example vascular endothelial growth factor, epithelial growth factor, platelet derived growth factor and hepatocyte growth factor such inhibitors include growth factor antibodies, growth factor receptor antibodies, tyrosine kinase inhibitors and serine/threonine kinase inhibitors);

(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan);

(iv) antiangiogenic agents that work by different mechanisms from those defined hereinbefore (for example receptor tyrosine kinases like Tie-2, inhibitors of integrin αvβ3 function, angiostatin, razoxin, thalidomide), and including vascular targeting agents; and (v) differentiation agents (for example retinoic acid and vitamin D).

According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts or in vivo hydrolysable esters or amides thereof, are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

For the benefit of the reader, where a pharmaceutical composition comprising a compound of formula (I), or the use of a compound of formula (I) as a medicament, or the use of a compound of formula (I) in a method of treatment, or the use of a compound of formula (I) in the manufacture of a medicament, or the use of a compound of formula (I) in the treatment of cancer, is described herein, it is to be understood that here, the definition of the compound of formula (I) includes the compounds N-(2-amino-6-hydroxyphenyl)-4-(1-methylhomopiperazin-4-yl)benzamide; N-(2-amino-6-methylphenyl)-4-(1-methylhomopiperazin-4-yl)benzamide; N-(2-aminophenyl)-4-(1-t-butoxycarbonylhomopiperazin-4-yl)benzamide; and N-(2-aminophenyl)-4-(1-methylhomopiperazin-4-yl)benzamide.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are not necessarily the maximum attainable;

(v) in general, the structures of the end-products of the Formula (I) were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the formula (I) were determined after crystallisation from a conventional organic solvent such as ethanol, methanol, acetone, ether or hexane, alone or in admixture;

(viii) the following abbreviations have been used:—
DMF N,N-dimethylformamide
DMSO dimethylsulphoxide
THF tetrahydrofuran

EXAMPLE 1

N-(2-Aminophenyl)-4-pyridin-4-ylbenzamide

N-(2-t-Butoxycarbonylaminophenyl)-4-pyridin-4-ylbenzamide (Method 1; 100 mg, 0.26 mmol), 1,4-dioxane (2 ml) and a 4M solution of hydrogen chloride in dioxane (2 ml) were stirred at ambient temperature for approximately 20 hours. The resultant precipitate was collected by filtration and washed with iso-hexane and diethyl ether and dried in vacuo to give the title compound as its hydrochloride (43 mg, 46%); NMR Spectrum: (DMSO-$d_6$) 7.31 (m, 2H), 7.39 (t, 1H), 7.54 (t, 1H), 8.17 (d, 2H), 8.30 (d, 2H), 8.40 (d, 2H), 8.96 (d, 2H), 10.62 (s, 1H); Mass Spectrum: M+H$^+$ 290.

EXAMPLE 2

Using an analogous procedure to that described in Example 1, the appropriate N-(2-t-butoxycarbonylaminophenyl)-benzamide starting material was reacted to give the compounds described in Table 1. Unless otherwise stated, each compound was obtained as its hydrochloride salt.

TABLE 1

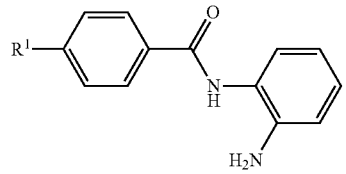

| Note | R$^1$ | Analytical Data | SM |
|---|---|---|---|
| 1 | quinolin-8-yl | NMR Spectrum: (DMSO-$d_6$) 7.37 (t, 1H), 7.49 (t, 1H), 7.62 (d, 1H), 7.78 (m, 5H), 7.93 (d, 1H), 8.18 (d, 1H), 8.31 (d, 2H), 8.72 (d, 1H), 9.04 (dd, 1H), 10.75 (s, 1H); Mass Spectrum: M + H$^+$ 340. | Meth 2 |
| 2 | pyridin-3-yl | NMR Spectrum: (DMSO-$d_6$) 7.32 (m, 2H), 7.43 (d, 1H), 7.57 (d, 1H), 7.95 (dd, 1H), 8.03 (d, 2H), 8.27 (d, 2H), 8.72 (d, 1H), 8.83 (d, 1H), 9.25 (s, 1H), 10.60 (s, 1H); Mass Spectrum: M + H$^+$ 290. | Meth 3 |
| 3 | pyridin-2-yl Formic acid salt | NMR Spectrum: (DMSO-$d_6$): 6.63 (t, 1H), 6.80 (d, 1H), 6.98 (t, 1H), 7.23 (d, 1H), 7.44 (t, 1H), 7.95 (t, 1H), 8.13 (m, 3H), 8.22 (d, 2H), 8.72 (d, 1H), 9.74 (s, 1H); Mass Spectrum: M + H$^+$ 290. | Meth 4 |
| 4 | 6-(methoxy)-1,2-pyrazin-3-yl | NMR Spectrum: (DMSO-$d_6$) 4.09 (s, 3H), 7.32 (m, 4H), 7.49 (m, 1H), 8.24 (m, 5H), 10.46 (s, 1H); Mass Spectrum: M + H$^+$ 321. | Meth 5 |
| 5 | furan-3-yl | NMR Spectrum: (DMSO-$d_6$) 7.09 (s, 1H), 7.25 (m, 3H), 7.58 (d, 1H), 7.83 (d, 3H), 8.06 (d, 2H), 8.33 (s, 1H), 10.32 (s, 1H); Mass Spectrum: M + H$^+$ 279. | Meth 6 |
| 6 | 2-methylpyridin-4-yl | NMR Spectrum: (DMSO-$d_6$) 2.82 (s, 3H), 7.21 (m, 1H), 7.29 (m, 2H), 7.51 (d, 2H), 8.20 (d, 2H), 8.31 (m, 3H), 8.41 (s, 1H), 8.89 (d, 1H), 10.51 (s, 1H); Mass Spectrum: M + H$^+$ 304. | Meth 7 |
| 7 | 2-fluoropyridin-4-yl | NMR Spectrum: (DMSO-$d_6$) 7.26-7.33 (m, 3H), 7.49 (d, 1H), 7.68 (s, 1H), 7.83 (m, 1H), 8.08 (d, 2H), 8.23 (d, 2H), 8.37 (d, 1H), 10.50 (s, 1H); Mass Spectrum: M + H$^+$ 308. | Meth 8 |
| 8 | thiazol-2-yl | NMR Spectrum: (DMSO-$d_6$) 7.39 (t, 1H), 7.48 (t, 1H), 7.56 (d, 1H), 7.64 (d, | Meth 9 |

TABLE 1-continued

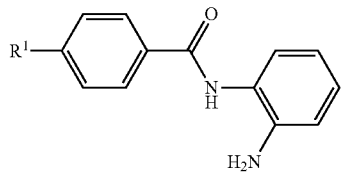

| Note | R¹ | Analytical Data | SM |
|---|---|---|---|
| | | 1H), 7.92 (d, 1H), 8.02 (d, 1H), 8.13 (d, 2H), 8.27 (d, 2H), 10.77 (s, 1H); Mass Spectrum: M + H⁺ 296. | |
| 9 | 2-amino-pyrimidin-6-yl | NMR Spectrum: (DMSO-d₆) 7.32 (m, 2H), 7.41 (m, 1H), 7.57 (m, 2H), 8.30 (m, 4H), 8.51 (d, 1H), 10.64 (s, 1H); Mass Spectrum: M + H⁺ 306. | Meth 10 |
| 10 | pyrimidin-6-yl | NMR Spectrum: (DMSO-d₆) 7.33 (m, 3H), 7.52 (m, 1H), 8.25 (m, 3H), 8.40 (d, 2H), 8.95 (d, 1H), 9.33 (s, 1H), 10.52 (s, 1H); Mass Spectrum: M + H⁺ 291. | Meth 11 |
| 11 | 2-chloro-pyrimidin-6-yl | NMR Spectrum: (DMSO-d₆) 7.39 (m, 2H), 7.46 (dd, 1H), 7.58 (dd, 1H), 8.30 (m, 3H), 8.39 (d, 2H), 8.93 (d, 1H), 10.72 (s, 1H); Mass Spectrum: M + H⁺ 325. | Meth 12 |

EXAMPLE 3

N-(2-Aminophenyl)-4-morpholinobenzamide

A solution of 1-(N-t-butoxycarbonylamino)-2-aminobenzene (Method 17; 104 mg, 0.5 mmol) in DMF (1.6 ml) was added to 4-morpholinobenzoic acid (149 mg, 0.5 mmol) followed by 4-(4,6-dimethoxy-1,3,5-triazinyl-2-yl)-4-methylmorpholinium chloride (Method 18, 138 mg, 0.5 mmol) and the reaction mixture stirred at ambient temperature for 48 hours. The solvent was removed in vacuo and the resultant residue partitioned between ethyl acetate and water. The organic phase was separated, then washed with water, brine and dried over sodium sulfate then filtered. The organic extracts were concentrated by half and a 4M solution of hydrogen chloride in 1,4-dioxane (1 ml) added. The reaction mixture was stirred at ambient temperature for a further 64 hours and the resultant precipitate was collected by filtration. This solid was purified by preparative mass triggered HPLC, eluting with an increasing gradient of acetonitrile in water (which contains 5% (v/v) of a 1% (v/v) solution of formic acid in methanol) to afford the title compound (17 mg, 12%); NMR Spectrum: (DMSO-d₆) 3.25 (m, 4H), 3.76 (m, 4H), 4.83 (s, 2H), 6.60 (m, 1H), 6.79 (dd, 1H), 6.96 (m, 1H), 7.01 (d, 2H), 7.16 (dd, 1H), 7.90 (d, 2H), 9.31 (brs, 1H); Mass Spectrum: M+H⁺ 298.

EXAMPLE 4

N-(2-Aminophenyl)-4-(1-methylpiperidin-4-yl)benzamide

N-(2-Aminophenyl)-4-piperidin-4-ylbenzamide (Example 5, 48 mg, 0.16 mmol) was stirred and dissolved in anhydrous DMF (2 ml) at ambient temperature. Potassium carbonate (23 mg, 0.16 mmol) was added followed by iodomethane (0.01 ml, 0.16 mmol) and the mixture stirred for 3 hours. The reaction mixture was diluted with water (20 ml) and extracted with ethyl acetate. The combined extracts were washed once with brine, dried over magnesium sulfate, filtered and the solvent evaporated to give the title compound as a colourless solid (16 mg, 32%); NMR Spectrum: (DMSO-d₆) 1.70 (m, 4H), 1.96 (m, 2H), 2.18 (s, 3H), 2.85 (m, 2H), 3.03 (m, 1H), 4.84 (b, 2H), 6.57 (m, 1H), 6.76 (d, 1H), 6.95 (m, 1H), 7.16 (d, 1H), 7.36 (d, 2H), 7.99 (d, 2H), 9.54 (b, 1H); Mass Spectrum: M+H⁺ 310.

EXAMPLE 5

N-(2-Aminophenyl)-4-piperidin-4-ylbenzamide

A 4M solution of hydrogen chloride in dioxane (5 ml, 20 mmol) was added to a stirred solution of N-(2-t-butoxycarbonylaminophenyl)-4-(1-t-butoxycarbonylpiperidin-4-yl) benzamide (Method 15, 693 mg, 1.40 mmol) in 1,4-dioxane (5 ml) and the mixture stirred at ambient temperature for 18 hours. The resultant precipitate was filtered and washed with diethyl ether. The resultant solid was dissolved in water and basified to pH 12 with 2M solution of aqueous sodium hydroxide. The resultant precipitate was filtered, washed with water and dried in vacuo to give the title compound (338 mg, 82%); NMR Spectrum: (DMSO-d₆) 1.52 (m, 2H), 1.69 (m, 2H), 2.60 (m, 3H), 3.02 (m, 2H), 4.84 (br, 2H), 6.58 (m, 1H), 6.76 (d, 1H), 6.95 (m, 1H), 7.16 (d, 1H), 7.34 (d, 2H), 7.89 (d, 2H), 9.53 (br, 1H); Mass Spectrum: M+H⁺ 296.

EXAMPLE 6

N-(2-Aminophenyl)-4-(1-methylpiperazin-4-yl)benzamide

N-(2-t-Butoxycarbonylaminophenyl)-4-(1-methylpiperazin-4-yl)benzamide (Method 16, 196 mg, 0.48 mmol) was dissolved in a 1M solution of hydrogen chloride in diethyl ether (7.2 ml, 7.2 mmol) and stirred at ambient temperature for 24 hours. The resultant precipitate was collected by filtration and washed with diethyl ether. To the solid was added a 2M solution of aqueous sodium hydroxide (5 ml) and the mixture extracted with ethyl acetate. The organic extract was dried over magnesium sulfate, filtered and evaporated to afford the title compound as a colourless solid (16 mg, 11%); NMR Spectrum: (CDCl₃) 2.36 (s, 3H), 2.57 (t, 4H), 3.33 (t, 4H), 3.88 (br, 2H), 6.81 (m, 2H), 6.91 (d, 2H) 7.06 (t, 1H), 7.27 (d, 1H), 7.79 (s, 1H), 7.80 (m, 2H); Mass Spectrum: M+H+ 311.

EXAMPLE 7

N-(2-Aminophenyl)-4-[2-(3-morpholinoaminopropyl)-pyrimidin-6-yl]benzamide

N-(2-Aminophenyl)-4-[2-(3-morpholinoaminopropyl)-pyrimidin-6-yl]benzamide trihydrochloride (Method 19, 28 mg, 0.052 mmol) was dissolved in water (2 ml) and basified to pH 10 by the of addition of 28% aqueous ammonium hydroxide solution (2 drops). The resultant precipitate was collected by filtration and dried under vacuum at 40° C. overnight to afford the title compound as a yellow solid (9 mg, 40%); NMR (DMSO-$d_6$): 1.75 (m, 2H), 2.37 (m, 6H), 3.41 (brm, 2H), 3.59 (m, 4H), 4.92 (s, 2H), 6.62 (t, 1H), 6.80 (d, 1H), 6.99 (t, 1H), 7.21 (m, 2H), 7.28 (t, 1H), 8.11 (d, 2H), 8.22 (d, 2H), 8.39 (d, 1H), 9.74 (s, 1H); Mass Spectrum: M+H+ 433.

EXAMPLE 8

N-(2-Aminophenyl)-4-[2-(3-morpholinoaminoethyl)-pyrimidin-6-yl]benzamide

N-(2-Aminophenyl)-4-[2-(3-morpholinoaminoethyl)-pyrimidin-6-yl]benzamide trihydrochloride (Method 24, 22 mg, 0.042 mmol) was reacted in an analogous manner to that described for Example 7 to afford the title compound as a pale yellow solid (12 mg, 68%); NMR (DMSO-$d_6$): 2.45 (m, 4H), 2.54 (m, 2H), 3.51 (m, 2H), 3.59 (m, 4H), 4.92 (s, 2H), 6.62 (t, 1H), 6.80 (d, 1H), 6.99 (t, 1H), 7.07 (t, 1H), 7.20 (d, 1H), 7.24 (d, 1H), 8.11 (d, 2H), 8.23 (d, 2H), 8.40 (d, 1H), 9.74 (s, 1H); Mass Spectrum: M+H+ 419.

EXAMPLE 9

Using an analogous procedure to that described in Example 1, the appropriate N-(2-t-butoxycarbonylaminophenyl)benzamide starting material was reacted to give the compounds described in Table 2. Unless otherwise stated, each compound was obtained as its hydrochloride salt.

TABLE 2

| Note | R[1] | Analytical Data | SM |
|---|---|---|---|
| 1 | piperidine-propyl-NH-pyrimidine-tBu | NMR Spectrum: (DMSO-$d_6$) 1.39 (m, 1H), 1.70 (m, 1H), 1.79 (m, 4H), 2.06 (m, 2H), 2.85 (m, 2H), 3.12 (m, 2H), 3.52 (m, 2H), 4.41 (d, 2H), 7.33 (m, 2H), 7.41 (m, 2H), 7.59 (m, 1H), 8.27 (d, 2H), 8.32 (d, 2H), 8.48 (d, 1H), 10.10 (s, 1H), 10.61 (s, 1H); Mass Spectrum: M + H+ 431. | Meth 29 |
| 2 | imidazole-propyl-NH-pyrimidine-tBu | NMR Spectrum: (DMSO-$d_6$) 2.17 (qn, 2H) 3.42 (m, 2H), 4.33 (t, 2H), 7.30 (m, 2H), 7.37 (m, 2H), 7.57 (m, 1H), 7.75 (brm, 2H), 7.85 (t, 1H), 8.26 (s, 4H), 8.45 (d, 1H), 9.21 (s, 1H), 10.56 (s, 1H); Mass Spectrum: M + H+ 414. | Meth 30 |
| 3 | N-methylpiperazine-propyl-NH-pyrimidine-tBu | NMR Spectrum: (DMSO-$d_6$) 2.08 (m, 2H), 2.84 (s, 3H), 3.28 (m, 2H), 3.49 (brm, 6H), 3.69 (brm, 4H), 7.32 (m, 2H), 7.40 (m, 2H), 7.57 (m, 1H), 7.74 (brm, 1H), 8.26 (d, 2H), 8.32 (m, 2H), 8.47 (d, 1H), 10.58 (s, 1H); Mass Spectrum: M + H+ 446. | Meth 31 |
| 4 | diethylamino-butyl-NH-pyrimidine-tBu | NMR Spectrum: (DMSO-$d_6$) 1.22 (t, 6H), 1.69 (m, 2H), 1.77 (m, 2H), 3.08 (m, 6H), 3.50 (m, 2H), 7.33 (m, 2H), 7.44 (m, 2H), 7.60 (m, 1H), 7.98 (brs, 1H), 8.30 (m, 4H), 8.48 (d, 1H), 10.12 (s, 1H), 10.64 (s, 1H); Mass Spectrum: M + H+ 433. | Meth 32 |

TABLE 2-continued

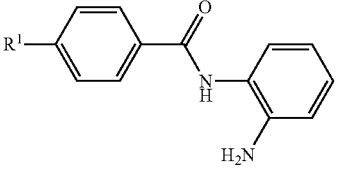

| Note | R¹ | Analytical Data | SM |
|---|---|---|---|
| 5 | 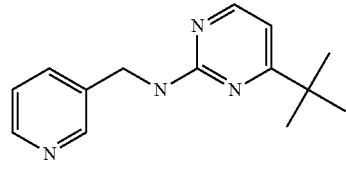 | NMR Spectrum: (DMSO-$d_6$) 1.25 (t, 6H), 3.22 (qn, 4H), 3.30 (q, 2H), 3.80 (brm, 2H), 7.32 (m, 2H), 7.40 (m, 2H), 7.56 (m, 1H), 7.61 (brs, 1H), 8.25 (d, 2H), 8.32 (d, 2H), 8.50 (d, 1H), 10.14 (brs, 1H), 10.57 (s, 1H); Mass Spectrum: M + H⁺ 405. | Meth 33 |
| 6 | 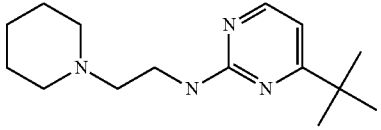 | NMR Spectrum: (DMSO-$d_6$) 4.82 (s, 2H), 7.35 (m, 2H), 7.41 (d, 1H), 7.45 (m, 1H), 7.59 (m, 1H), 8.02 (dd, 1H), 8.19 (brs, 1H), 8.42 (s, 4H), 8.48 (m, 1H), 8.58 (m, 1H), 8.81 (d, 1H), 8.92 (s, 1H), 10.62 (s, 1H); Mass Spectrum: M + H⁺ 397. | Meth 34 |
| 7 | 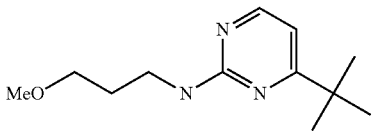 | NMR Spectrum: (DMSO-$d_6$) 1.41 (m, 1H), 1.73 (m, 1H), 1.80 (m, 4H), 2.95 (m, 2H), 3.30 (m, 2H), 3.54 (m, 2H), 3.81 (m, 2H), 7.30 (m, 2H), 7.35 (m, 1H), 7.40 (d, 1H), 7.53 (d, 1H), 7.63 (brs, 1H), 8.24 (d, 2H), 8.31 (d, 2H), 8.49 (d, 1H), 9.93 (brs, 1H), 10.51 (s, 1H); Mass Spectrum: M + H⁺ 417. | Meth 35 |
| 8 | 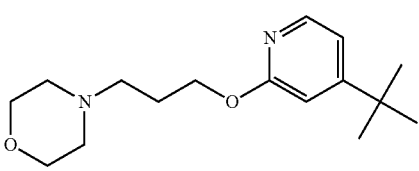 | NMR Spectrum: (DMSO-$d_6$) 1.86 (qn, 2H), 3.26 (s, 3H), 3.45 (t, 2H), 3.50 (brm, 2H), 7.32 (m, 2H), 7.39 (m, 2H), 7.54 (m, 1H), 8.24 (d, 2H), 8.33 (d, 2H), 8.47 (d, 1H), 10.56 (s, 1H); Mass Spectrum: M + H⁺ 378. | Meth 36 |
| 9 | 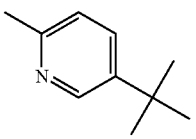 | NMR Spectrum: (DMSO-$d_6$) 2.25 (m, 2H) 3.08 (m, 2H), 3.27 (m, 2H), 3.45 (d, 2H), 3.85 (t, 2H), 3.97 (m, 2H), 4.43 (t, 2H), 7.24 (s, 1H), 7.36 (t, 1H), 7.43 (t, 1H), 7.44 (d, 1H), 7.51 (d, 1H), 7.62 (d, 1H), 7.98 (d, 2H), 8.27 (d, 2H), 8.29 (d, 1H), 10.67 (s, 1H), 11.26 (s, 1H); Mass Spectrum: M + H⁺ 433. | Meth 37 |
| 10 | 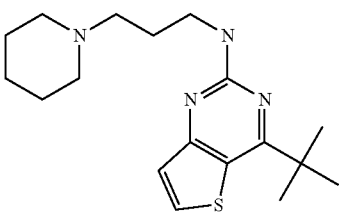 | NMR Spectrum: (DMSO-$d_6$) 2.76 (s, 3H), 7.28 (m, 3H), 7.51 (d, 1H), 7.93 (d, 1H), 8.05 (d, 2H), 8.27 (d, 2H), 8.75 (d, 1H), 9.17 (s, 1H), 10.46 (s, 1H); Mass Spectrum: M + H⁺ 304. | Meth 38 |
| 11 |  | NMR Spectrum: (DMSO-$d_6$) 1.36 (m, 1H), 1.78-1.66 (m, 5H) 2.05 (m, 2H), 2.86 (q, 2H), 3.13 (m, 2H), 3.57 (m, 4H), 7.36 (m, 4H), 7.53 (d, 1H), 8.23 (d, 2H), 8.32 (d, 2H), 8.37 (d, 1H), 9.78 (brs, 1H) 10.59 (s, 1H); Mass Spectrum: M + H⁺ 487. | Meth 39 |

TABLE 2-continued

| Note | R¹ | Analytical Data | SM |
|---|---|---|---|
| 12 | thieno[3,2-d]pyrimidin-4-yl tert-butyl | NMR Spectrum: (DMSO-d$_6$) 7.39 (t, 1H), 7.45 (t, 1H), 7.51 (d, 1H), 7.63 (d, 1H), 7.80 (d, 1H), 8.34 (d, 2H), 8.39 (d, 2H), 8.65 (d, 1H), 9.35 (s, 1H), 10.77 (s, 1H); Mass Spectrum: M + H⁺ 347. | Meth 40 |
| 13 | 2-(3-piperidin-1-ylpropylamino)-5-tert-butylpyrimidin-2-yl | NMR Spectrum (DMSO-d$_6$): 1.39 (m, 1H), 1.70 (m, 1H), 1.78 (m, 4H), 2.02 (m, 2H), 2.86 (m, 2H), 3.08 (m, 2H), 3.42 (m, 4H), 7.37 (m, 2H), 7.48 (d, 1H), 7.61 (d, 1H), 7.86 (d, 2H), 8.21 (d, 2H), 8.81 (s, 2H), 10.17 (s, 1H), 10.56 (s, 1H); Mass Spectrum: M + H⁺ 431. | Meth 41 |
| 14 | 2-(3-(4-methylpiperazin-1-yl)propylamino)-5-tert-butylpyrimidin-2-yl | NMR Spectrum (DMSO-d$_6$): 2.03 (m, 2H), 2.82 (t, 3H), 3.23 (t, 2H), 3.45 (m, 6H), 3.67 (m, 4H), 7.34 (t, 1H), 7.42 (t, 1H), 7.50 (d, 1H), 7.62 (d, 1H), 7.85 (d, 2H), 8.21 (d, 2H), 8.81 (s, 2H), 10.60 (s, 1H); Mass Spectrum: M + H⁺ 446. | Meth 42 |
| 15 | 2-(3-morpholinopropylamino)-5-tert-butylpyrimidin-2-yl | NMR Spectrum (DMSO-d$_6$): 2.00 (m, 2H), 3.08 (m, 2H), 3.18 (m, 2H), 3.43 (m, 4H), 3.87 (m 2H), 4.00 (m, 2H), 7.34 (m, 2H), 7.42 (d, 1H) 7.58 (d, 1H), 7.87 (d, 2H), 8.19 (d, 2H), 8.82 (s, 2H), 10.46 (s, 1H), 10.82 (s, 1H); Mass Spectrum: M + H⁺ 433. | Meth 43 |
| 16 | 2-(2-pyrrolidin-1-ylethoxy)-5-tert-butylpyrimidin-2-yl | NMR Spectrum (DMSO-d$_6$): 1.91 (m, 2H), 2.05 (m, 2H), 3.13 (m, 2H), 3.68 (m, 4H), 4.75 (t, 2H), 7.36 (m, 2H), 7.47 (d, 1H), 7.60 (d, 1H), 8.00 (d, 2H), 8.26 (d, 2H), 9.11 (s, 2H), 10.60 (s, 1H), 10.80 (s, 1H); Mass Spectrum: M + H⁺ 404. | Meth 45 |
| 17 | 2-(3-morpholinopropylamino)-4-tert-butylthieno[3,2-d]pyrimidin-2-yl | NMR Spectrum: 2.10 (m, 2H), 3.06 (m, 2H), 3.21 (M, 2H), 3.43 (d, 2H), 3.55 (m, 2H), 3.84 (m, 2H), 3.94 (m, 2H), 7.37 (m, 2H), 7.42 (m, 1H), 7.51 (d, 1H), 7.64 (d, 1H), 8.23 (d, 2H), 8.37 (d 2H), 8.40 (d, 1H), 10.75, (s, 1H), 11.10 (brs, 1H); Mass Spectrum: M + H⁺ 489. | Meth 65 |

TABLE 2-continued

| Note | R¹ | Analytical Data | SM |
|---|---|---|---|
| 18 | (2-(piperidin-1-yl)ethyl)amino-4-tert-butylthieno[3,2-d]pyrimidin-2-yl | NMR Spectrum: (DMSO-d₆) 1.41 (m, 1H), 1.72 (m, 1H), 1.80 (m, 4H), 2.96 (m, 2H), 3.32 (q, 2H), 3.57 (m, 2H), 3.83 (m, 2H), 7.34 (m, 2H), 7.38 (d, 1H), 7.41 (m, 1H), 7.58 (m, 1H), 8.25 (d, 2H), 8.35 (d, 2H), 8.39 (d, 1H), 9.92 (s, 1H), 10.63 (s, 1H); Mass Spectrum: M + H⁺ 474. | Meth 66 |
| 19 | cyclohexylcarbamate of (2-tert-butylthiazol-5-yl)methanol | NMR Spectrum: (DMSO-d₆): 1.20 (m, 5H), 1.54 (d, 1H), 1.69 (d, 2H), 1.78 (d, 2H), 3.30 (m, 1H), 5.28 (s, 2H), 7.29 (d, 1H), 7.38 (t, 1H), 7.44 (t, 1H), 7.52 (d, 1H), 7.62 (d, 1H), 8.00 (s, 1H), 8.10 (d, 2H), 8.25 (d, 2H), 10.66 (s, 1H); Mass Spectrum: M + H⁺ 451. | Meth 67 |
| 20 | 4-(5-tert-butylthiophen-2-yl)-2-(methylthio)pyrimidine | NMR Spectrum: (DMSO-d₆): 2.59 (s, 3H), 4.93 (s, 2H), 6.62 (t, 1H), 6.81 (d, 1H), 7.01 (t, 1H), 7.20 (d, 1H), 7.75 (d, 1H), 7.84 (d, 1H), 7.94 (d, 2H), 8.08 (d, 2H), 8.15 (d, 1H), 8.65 (d, 1H), 9.75 (s, 1H); Mass Spectrum: M + H⁺ 419 | Meth 68 |
| 21 | 7-tert-butylthieno[3,2-b]pyridine | NMR Spectrum: (DMSO-d₆) 7.34 (t, 1H), 7.44 (t, 1H), 7.60 (d, 1H), 7.70 (d, 1H), 7.96 (m, 2H), 8.10 (d, 2H), 8.44 (d, 2H), 8.67 (m, 1H), 9.08 (m, 1H), 10.88 (s, 1H); Mass Spectrum: M + H⁺ 346. | Meth 74 |
| 22 | 4-tert-butylthieno[3,2-d]pyrimidine | NMR Spectrum: (DMSO-d₆) 7.37 (m, 1H), 7.43 (t, 1H), 7.49 (dd, 1H), 7.61 (dd, 1H), 7.76 (d, 1H), 8.11 (d, 1H), 8.17 (d, 2H), 8.33 (d, 2H), 9.21 (s, 1H), 10.73 (s, 1H); Mass Spectrum: M + H⁺ 347. | Meth 75 |

EXAMPLE 10

Using an analogous procedure to that described in Example 1, the appropriate N-(2-t-butoxycarbonylaminophenyl)benzamide starting material was reacted to give the compounds described in Table 3. Unless otherwise stated, each compound was obtained as its hydrochloride salt.

TABLE 3

[Structure: fluorobenzamide with R¹ substituent, N-(2-aminophenyl) group]

| | R¹ | Analytical Data | SM |
|---|---|---|---|
| 1 | 3-pyridyl | NMR Spectrum: (DMSO-d$_6$): 7.40 (m, 2H), 7.50 (d, 1H), 7.63 (d, 1H), 7.91 (t, 1H), 7.99 (t, 1H), 8.18 (m, 2H), 8.58 (d, 1H), 8.89 (d, 1H), 9.10 (s, 1H), 10.76 (s, 1H); Mass Spectrum: M + H⁺ 308. | Meth 44 |

EXAMPLE 11

Using an analogous procedure to that described in Example 7, the appropriate N-(2-aminophenyl)-benzamide hydrochloride salt starting material was reacted to give the compounds described in Table 4. Unless otherwise stated, each compound was obtained as its free base.

TABLE 4

[Structure: benzamide with R¹ substituent, N-(2-aminophenyl) group]

| Note | R¹ | Analytical Data | SM |
|---|---|---|---|
| 1 | [morpholine-propyl-N-pyridin-2-yl group] | NMR Spectrum: (DMSO-d$_6$) 1.74 (m, 2H), 2.42 (brm, 4H), 3.34 (m, 4H), 3.60 (m, 4H), 4.91 (s, 2H), 6.62 (t, 2H), 6.81 (m, 3H), 6.99 (t, 1H), 7.20 (d, 1H), 7.79 (d, 2H), 8.09 (m, 3H), 9.72 (s, 1H); Mass Spectrum: M + H⁺ 432. | Meth 46 |
| 2 | [1-methyl-imidazo-pyrimidine with t-butyl] | NMR Spectrum: (DMSO-d$_6$) 3.92 (s, 3H), 5.00 (brs, 2H), 6.63 (t, 1H), 6.82 (d, 1H), 7.01 (m, 1H), 7.23 (d, 1H), 8.20 (d, 2H), 8.70 (s, 1H), 8.98 (d, 2H), 9.06 (s, 1H), 9.82 (s, 1H); Mass Spectrum: M + H⁺ 345. | Meth 47 |
| 3 | [piperazinyl-pyrazinyl with t-butyl] | NMR Spectrum: (DMSO-d$_6$) 2.84 (m, 4H), 3.61 (m, 4H), 4.62 (s, 2H), 6.62 (t, 1H), 6.80 (d, 1H), 6.99 (t, 1H), 7.21 (d, 1H), 8.09 (d, 2H), 8.21 (d, 2H), 8.31 (s, 1H), 8.53 (s, 1H), 9.72 (s, 1H); Mass Spectrum: M + H⁺ 375. | Meth 48 |

TABLE 4-continued

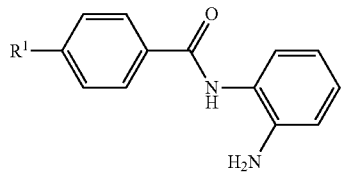

| Note | R¹ | Analytical Data | SM |
|---|---|---|---|
| 4 | (N,N-diethyl-6-tert-butyl-1,3,5-triazin-2-yl) | NMR Spectrum: (DMSO-d$_6$@ 373K) 1.22 (t, 6H) 3.43 (qn, 4H), 4.72 (brs, 2H), 6.65 (t, 1H), 6.83 (d, 1H), 6.90 (m, 2H), 7.01 (t, 1H), 7.28 (d, 1H), 8.06 (d, 2H), 8.39 (d, 2H), 9.44 (s, 1H); Mass Spectrum: M + H$^+$ 378. | Meth 49 |
| 5 | (4-methylpiperazin-1-yl)-4-tert-butylpyrimidin-2-yl | NMR Spectrum: (DMSO-d$_6$) 2.26 (s, 3H), 2.43 (m, 4H), 3.86 (m, 4H), 4.92 (s, 2H), 6.62 (t, 1H), 6.81 (d, 1H), 6.99 (t, 1H), 7.20 (d, 1H), 7.31 (d, 1H), 8.11 (d, 2H), 8.26 (d, 2H), 8.50 (d, 1H), 9.75 (s, 1H); Mass Spectrum: M + H$^+$ 389. | Meth 50 |

EXAMPLE 12

N-(2-aminophenyl)-4-[5-(piperidin-1-ylmethyl)-1,3-thiazol-2-yl]benzamide

N-(2-t-butoxycarbonylaminophenyl)-4-[5-(piperidin-1-ylmethyl)-1,3-thiazol-2-yl]benzamide (Method 51, 271 mg, 0.54 mmol) was suspended in 1,4 dioxane (4 ml) and a 4M solution of hydrogen chloride in 1,4-dioxane (4 ml) added. The reaction mixture was stirred at ambient temperature for 17 hours. The resultant precipitate was collected by filtration, washed with diethyl ether and air dried to yield the title compound as its hydrochloride salt. The crude solid was purified using an Oasis MCX column, eluting with methanol/dichloromethane (0-100%) then 2M ammonia in methanol/methanol (0-20%) to give the title compound as its free base (119 mg, 56%); NMR Spectrum: (DMSO-d$_6$) 1.40 (m, 2H), 1.50 (m, 4H), 2.41 (m, 4H), 3.74 (s, 2H), 4.94 (s, 2H), 6.61 (t, 1H), 6.80 (d, 1H), 6.99 (t, 1H), 7.18 (d, 1H), 7.80 (s, 1H), 8.06 (d, 2H), 8.09 (d, 2H), 9.78 (s, 1H); Mass Spectrum: M+H$^+$ 402.

EXAMPLE 13

N-(2-aminophenyl)-4-[2-({3-[2-(dimethylamino)ethoxy]propyl}amino)pyrimidin-4-yl]benzamide To a solution of dimethylaminoethoxypropylamine (2.02 mg, 12.5 µmol) in N,N-dimethylacetamide (125 µl), was added a solution of N-(2-aminophenyl)-4-[2-(methylsulfonyl)pyrimidin-4-yl]benzamide (Method 62, 2.2 mg, 5 mop in N,N-dimethylacetamide (100 µl). The reaction mixture was heated to 50° C. and agitated for a period of 16 hours, before being evaporated to dryness to give the title compound; Mass Spectrum: M+H$^+$ 435.

EXAMPLE 14

Using an analogous procedure to that described in Example 13, N-(2-aminophenyl)-4-[2-(methylsulfonyl)pyrimidin-4-yl]benzamide (Method 62) was reacted with the appropriate amine to give the compounds described in Table 5.

TABLE 5

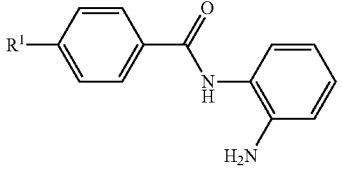

| Note | R¹ | Analytical Data | SM |
|---|---|---|---|
| 1 | 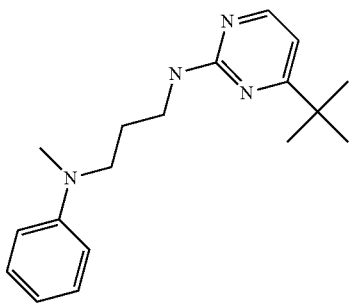 | Mass Spectrum: M + H⁺ 453. | CAS 53485-07-7 |
| 2 | 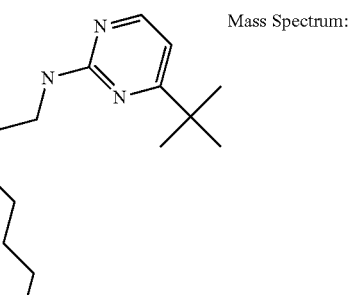 | Mass Spectrum: M + H⁺ 461. | CAS 3529-09-7 |

EXAMPLE 15

Using an analogous procedure to that described in Example 5, the appropriate N-(2-aminophenyl)benzamide hydrochloride salt starting material was reacted to give the compounds described in Table 6. Unless otherwise stated, each compound was obtained as its free base.

EXAMPLE 16

N-(2-aminophenyl)-4-piperazin-1-ylbenzamide

To a solution of 4-(4-t-butoxycarbonylpiperazin-1-yl)benzoic acid (1.0 g, 3.3 mmol) and 1-(t-butoxycarbonylamino)-2-aminobenzene (Method 17, 0.68 g, 3.3 mmol) in DMF (10

TABLE 6

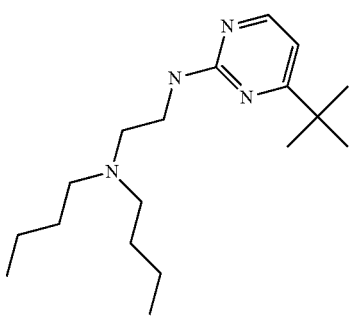

| Note | R¹ | Analytical Data | SM |
|---|---|---|---|
| 1 | 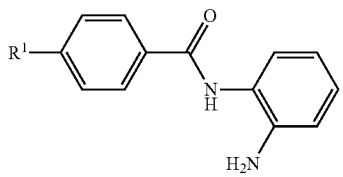 | NMR Spectrum: (DMSO-d₆): 4.93 (s, 2H), 5.46 (s, 2H), 6.62 (t, 1H), 6.80 (d, 1H), 7.01 (m, 2H), 7.21 (d, 1H), 7.32 (m, 2H), 7.50 (d, 2H), 8.10 (m, 5H), 9.78 (s, 1H), 9.83 (s, 1H); Mass Spectrum: M + H⁺ 445 | Meth 70 | ml) was added 4-(4,6-dimethoxy-1,3,5-triazinyl-2-yl)-4-methylmorpholinium chloride (1.1 g, 4.0 mmol) (Method 18). The mixture was stirred at ambient temperature for 20 hours. The mixture was concentrated in vacuo and the residue partitioned between water and ethyl acetate. The organic phase was separated and the aqueous reextracted with ethyl acetate. The combined organic extracts were dried over magnesium sulfate and evaporated. The residue was purified by flash chromatography (eluting with 4:1-1:1 isohexane/ethyl acetate). The product was dissolved in 1,4-dioxane (2.5 ml) and treated with a 4M solution of hydrogen chloride in 1,4-dioxane (2.5 ml). The mixture was stirred at ambient temperature for 4 hours. The resulting solid was collected by filtration, trated with a 2M aqueous solution of sodium hydroxide and extracted with ethyl acetate. The organic extract was dried over magnesium sulfate to afford the title compound as a colourless solid (176 mg, 92%); NMR Spectrum: (DMSO-$d_6$) 2.89 (t, 4H), 3.25 (t, 4H), 4.90 (s, 2H), 6.66 (t, 1H), 6.84 (d, 1H), 7.01 (m, 3H), 7.21 (d, 1H), 7.92 (d, 2H), 9.48 (s, 1H); Mass Spectrum: M+H$^+$ 297.

EXAMPLE 17

(RS)—N-(2-aminophenyl)-4-piperidin-3-ylbenzamide

To a solution of N-(2-t-butoxycarbonylaminophenyl)-4-pyridin-3-ylbenzamide (2.0 g, 5.1 mmol) (Method 3) in ethanol (20 ml) was added PtO$_2$ (200 mg) and the resulting mixture was heated at 80° C. under an atmosphere of hydrogen at 80 Bar for 16 hours. The mixture was allowed to cool and was filtered and evaporated to afford (RS)—N-(2-t-butoxycarbonylaminophenyl)-4-piperidin-3-ylbenzamide (1.9 g, 94%).

To a solution of (RS)—N-(2-t-butoxycarbonylaminophenyl)-4-piperidin-3-ylbenzamide (1.0 g, 2.5 mmol) in 1,4-dioxane (9.5 ml) was added a solution of hydrogen chloride (4M in 1,4-dioxane, 9.5 ml, 38 mmol) and the mixture stirred at ambient temperature for 6 hours. The solid formed was collected by filtration, washed with diethyl ether and dried in vacuo. It was treated with a 2M solution of aqueous sodium hydroxide and extracted three times with ethyl acetate. The combined organic extracts were dried over magnesium sulfate and evaporated to afford the product as a colourless solid (0.73 g, 99%); NMR Spectrum: (DMSO-$d_6$) 1.71 (m, 4H), 2.61 (m, 2H), 2.75 (m, 1H), 3.03 (m, 2H), 4.92 (s, 2H), 6.65 (t, 1H), 6.83 (d, 1H), 7.02 (t, 1H), 7.23 (d, 1H), 7.42 (d, 2H), 7.96 (d, 2H), 9.61 (s, 1H); Mass Spectrum: M+H$^+$ 296.

EXAMPLE 18

N-(2-aminophenyl)-4-(1,2,3,6-tetrahydropyridin-4-yl)benzamide dihydrochloride t-Butyl 4-{4-[({2-[(t-butoxycarbonyl)amino]phenyl}amino)carbonyl]phenyl}-3,6-dihydropyridine-1(2H)-carboxylate (Method 71, 62 mg, 0.13 mmol) was stirred and dissolved in 1,4-dioxane (0.4 ml) and a 4M solution of hydrogen chloride in 1,4-dioxane (0.4 ml) added. The reaction mixture was stirred at ambient temperature for 24 hours. The resultant precipitate was collected by filtration, washed with diethyl ether and dried in vacuo at 60° C. to yield the title compound as an off white solid (34 mg, 89%); NMR Spectrum: (DMSO-$d_6$) 2.70 (m, 2H), 3.30 (m, 2H), 3.76 (m, 2H), 6.33 (m, 1H), 7.23 (m, 2H), 7.33 (m, 1H), 7.49 (m, 1H), 7.61 (d, 2H), 8.10 (d, 2H), 9.27 (s, 1H); Mass Spectrum: M+H$^+$ 294.

EXAMPLE 19

N-(2-aminophenyl)-4-(1-{3-[(2-fluorophenyl)amino]-3-oxopropyl}piperidin-4-yl)benzamide N-(2-aminophenyl)-4-piperidine-4-ylbenzamide (Example 5, 162 mg, 0.55 mmol), potassium carbonate (153 mg, 1.1 mmol) and (2-fluorophenyl)-3-bromopropionamide (149 mg, 0.61 mmol) in DMF (5 ml) were stirred at ambient temperature for approximately 20 hours. The mixture was concentrated in vacuo and the residue partitioned between water and ethyl acetate. The organic layer was separated, dried over magnesium sulfate and evaporated. The residue was purified by flash chromatography (eluting with 0-25% methanol/dichloromethane to afford the product as a colourless solid (76 mg, 30%); NMR Spectrum: (CDCl$_3$) 1.92 (m, 4H), 2.18 (m, 1H), 2.57 (t, 2H), 2.64 (m, 2H) 2.72 (t, 2H), 3.19 (d, 2H), 3.62 (s, 2H), 6.80 (m, 2H), 7.05 (m, 4H), 7.31 (d, 1H), 7.34 (d, 2H), 7.87 (d, 2H), 8.08 (s, 1H), 8.44 (t, 1H), 11.39 (s, 1H); Mass Spectrum: M+H$^+$ 461.

EXAMPLE 20

4-(1-acetylpiperidin-4-yl)-N-(2-aminophenyl)benzamide

N-(2-aminophenyl)-4-piperidin-4-ylbenzamide (Example 5, 30 mg, 0.10 mmol) was stirred and dissolved in N,N-dimethylacetamide (2 ml) and acetic anhydride (0.011 ml, 0.11 mmol) added. The reaction was stirred at ambient temperature for 1 hour and then partitioned between water and ethyl acetate. The organic layer was separated, washed with brine and dried over magnesium sulfate, filtered and evaporated to give the title compound as a colourless solid (23 mg, 68%); NMR Spectrum: (DMSO-$d_6$) 1.48 (m, 1H), 1.64 (m, 1H), 1.79 (m, 2H), 2.02 (s, 3H), 2.59 (m, 1H), 2.84 (m, 1H), 3.13 (m, 1H), 3.92 (d, 1H), 4.53 (d, 1H), 4.85 (s, 2H), 6.58 (m, 1H), 6.76 (d, 1H), 6.95 (m, 1H), 7.15 (d, 1H), 7.37 (d, 2H), 7.90 (d, 2H), 9.55 (s, 1H); Mass Spectrum: M+H$^+$ 338.

EXAMPLE 21

Using an analogous procedure to that described in Example 19, N-(2-aminophenyl)-4-piperidin-4-ylbenzamide (Example 5) was reacted to give the compounds described in Table 7.

TABLE 7

[Structure: R¹-N-piperidine-phenyl-C(=O)-NH-phenyl-NH₂ (ortho)]

| Note | R¹ | Analytical Data | SM |
|---|---|---|---|
| 1 | tert-butyl carbamate with (CH₂)₂-C(CH₃)₂-CH₂- linker | NMR Spectrum: (DMSO-d₆) 1.39 (s, 9H), 1.59 (m, 2H), 1.71 (m, 2H), 1.78 (m, 2H), 2.02 (m, 2H), 2.34 (m, 2H), 2.61 (m, 1H), 2.98 (m, 4H), 4.87 (s, 2H), 6.60 (t, 1H), 6.78 (d, 1H), 6.83 (s, 1H), 6.97 (t, 1H), 7.17 (d, 1H), 7.38 (d, 2H), 7.91 (d, 2H), 9.56 (s, 1H); Mass Spectrum: M + H⁺ 453. | |
| 2 | benzyl with C(CH₃)₂-CH₂- linker | NMR Spectrum: (DMSO-d₆) 1.73 (m, 4H), 2.07 (m, 2H), 2.53 (m, 1H), 2.92 (m, 2H), 3.51 (s, 2H), 4.85 (s, 2H), 6.56 (t, 1H), 6.76 (d, 1H), 6.95 (t, 1H), 7.15 (d, 1H), 7.31 (m, 7H), 7.89 (d, 2H), 9.53 (s, 1H); Mass Spectrum: M + H⁺ 386. | |
| 3 | (S)-5-oxopyrrolidin-2-yl with CH₂-C(CH₃)₂-CH₂- linker | NMR Spectrum: (DMSO-d₆) 1.73 (m, 4H), 2.37 (m, 7H), 2.98 (t, 2H), 3.30 (m, 2H), 3.71 (m, 1H), 4.88 (s, 2H), 6.60 (t, 1H), 6.78 (d, 1H), 6.97 (t, 1H), 7.16 (d, 1H), 7.38 (d, 2H), 7.55 (s, 1H), 7.91 (d, 2H), 9.58 (s, 1H); Mass Spectrum: M + H⁺ 393. | |
| 4 | 2-methoxyphenoxy with -CH₂-CH₂-C(CH₃)₂-CH₂- linker | NMR Spectrum: (DMSO-d₆) 1.73 (m, 4H), 2.18 (t, 2H), 2.59 (m, 1H), 2.75 (t, 2H), 3.09 (d, 2H), 3.76 (s, 3H), 4.09 (t, 2H), 4.89 (s, 2H), 6.60 (t, 1H), 6.79 (d, 1H), 6.89 (m, 2H), 6.99 (m, 3H), 7.18 (d, 1H), 7.39 (d, 2H), 7.92 (d, 2H), 9.60 (s, 1H); Mass Spectrum: M + H⁺ 446. | |
| 5 | phenoxy with -CH₂-CH₂-C(CH₃)₂-CH₂- linker | NMR Spectrum: (CDCl₃) 1.88 (m, 4H), 2.29 (m, 2H), 2.62 (m, 1H), 2.90 (t, 2H), 3.18 (m, 2H), 3.89 (s, 2H), 4.18 (t, 2H), 6.86 (m, 2H), 6.96 (m, 3H), 7.11 (t, 1H), 7.31 (m, 5H), 7.86 (d, 2H), 7.90 (s, 1H); Mass Spectrum: M + H⁺ 416. | |
| 6 | 4-acetamidophenoxy with -CH₂-CH₂-C(CH₃)₂-CH₂- linker | NMR Spectrum: (DMSO-d₆) 1.73 (m, 4H), 2.00 (s, 3H), 2.16 (t, 2H), 2.46 (m, 1H), 2.72 (t, 2H), 3.07 (m, 2H), 4.06 (t, 2H), 4.89 (s, 2H), 6.59 (t, 1H), 6.78 (d, 1H), 6.89 (d, 2H), 6.96 (t, 1H), 7.17 (d, 1H), 7.39 (d, 2H), 7.47 (d, 2H), 7.91 (d, 2H), 9.58 (s, 1H), 9.77 (s, 1H); Mass Spectrum: M + H⁺ 473. | CAS no 57011-90-2 Justus Liebigs Ann. Chem. 1899, 287. DE 85988 |

TABLE 7-continued

| Note | R¹ | Analytical Data | SM |
|---|---|---|---|
| 7 | (1,2,3,4-tetrahydroquinolin-1-yl)-3,3-dimethylbutan-1-one group | NMR Spectrum: (DMSO-d$_6$) 1.61 (m, 2H), 1.74 (m, 2H), 2.20 (t, 2H), 2.67 (m, 1H), 2.73 (t, 2H), 2.92 (m, 2H), 3.27 (m, 2H), 3.34 (s, 2H), 3.75 (t, 2H), 4.86 (s, 2H), 6.60 (t, 1H), 6.78 (d, 1H), 6.97 (t, 1H), 7.09 (t, 1H), 7.18 (m, 3H), 7.35 (d, 2H), 7.60 (m, 1H), 7.91 (d, 2H), 9.55 (s, 1H); Mass Spectrum: M + H⁺ 470. | Method 73 |
| 8 | 4-chlorophenoxy-3,3-dimethylbutyl group | NMR Spectrum: (DMSO-d$_6$) 1.73 (m, 4H), 2.16 (m, 2H), 2.60 (m, 1H), 2.74 (t, 2H), 3.07 (m, 2H), 4.10 (t, 2H), 4.88 (s, 2H), 6.60 (t, 1H), 6.78 (d, 1H), 6.98 (m, 3H), 7.17 (d, 1H), 7.33 (d, 2H), 7.39 (d, 2H), 7.91 (d, 2H), 9.56 (s, 1H); Mass Spectrum: M + H⁺ 450. | |
| 9 | 2-(pyridin-2-yl)-3,3-dimethylbutyl group | NMR Spectrum: (DMSO-d$_6$) 1.75 (m, 4H), 2.18 (m, 2H), 2.61 (m, 1H), 2.96 (m, 2H), 4.86 (s, 2H), 6.60 (t, 1H), 6.79 (d, 1H), 6.97 (t, 1H), 7.18 (d, 1H), 7.27 (t, 1H), 7.39 (d, 2H), 7.48 (d, 1H), 7.78 (t, 1H), 7.92 (d, 2H), 8.50 (d, 1H), 9.56 (s, 1H); Mass Spectrum: M + H⁺ 388. | |
| 10 | 4-cyanophenyl-3,3-dimethylbutyl group | Mass Spectrum: M + H⁺ 411 | |
| 11 | 3-cyanophenyl-3,3-dimethylbutyl group | Mass Spectrum: M + H⁺ 411 | |
| 12 | (5-methoxypyridin-2-yl)-3,3-dimethylbutyl group | Mass Spectrum: M + H⁺ 416 | |
| 13 | tert-butyl (3,3-dimethylbutyl)carbamate group | Mass Spectrum: M + H⁺ 439 | |

TABLE 7-continued

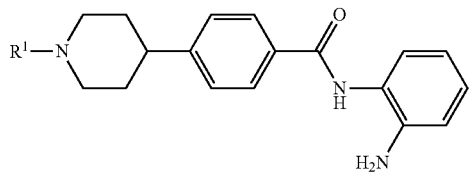

| Note | R¹ | Analytical Data | SM |
|---|---|---|---|
| 14 | (2-methoxyethoxy)-neopentyl | Mass Spectrum: M + H⁺ 412 | |
| 15 | 2,2-dimethyl-propyl-diol | Mass Spectrum: M + H⁺ 370 | |
| 16 | (tetrahydrofuran-2-yl)methyl-neopentyl | Mass Spectrum: M + H⁺ 380 | |
| 17 | benzyloxy-neopentyl | Mass Spectrum: M + H⁺ 444 | |
| 18 | pyrrol-1-yl-neopentyl | Mass Spectrum: M + H⁺ 403 | |
| 19 | acetoxy-neopentyl | Mass Spectrum: M + H⁺ 382 | |

EXAMPLE 22

N-(2-aminophenyl)-4-[1-(4-bromobenzoyl)piperidin-4-yl]benzamide

To a solution of 4-bromobenzoic acid (1.0 g, 3.3 mmol) in DMF (5 ml) was added benzotriazolyloxytripyrrolidinophosphonium hexafluorophosphate (99 mg, 0.19 mmol) and the mixture stirred at ambient temperature for 30 minutes. N-(2-aminophenyl)-4-piperidin-4-ylbenzamide (Example 5, 50 mg, 0.17 mmol) was added and the mixture stirred for a further 24 hours. The resulting solution was absorbed onto an SCX-2 column, washed with methanol (2 column volumes) and eluted with a 2M solution of ammonia in methanol (2 column volumes) to afford the product. This was purified by flash chromatography (eluting with 0-20% methanol/dichloromethane) to afford the title compound as a colourless solid (29 mg, 18%); NMR Spectrum: (DMSO-$d_6$) 1.70 (m, 4H), 2.60 (m, 1H), 2.91 (m, 2H), 3.31 (m, 2H), 4.89 (s, 2H), 6.60 (t, 1H), 6.78 (d, 1H), 6.97 (t, 1H), 7.16 (d, 1H), 7.43 (d, 4H), 7.67 (d, 2H), 7.93 (d, 2H), 9.60 (s, 1H); Mass Spectrum: M+H⁺ 478.

EXAMPLE 23

Using an analogous procedure to that described in Example 19, (RS)—N-(2-aminophenyl)-4-piperidin-3-yl-benzamide was reacted to give the compounds described in Table 8.

TABLE 8

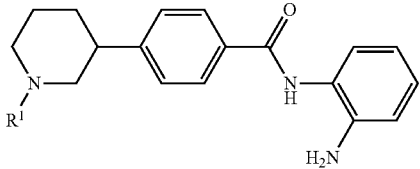

| Note | R¹ | Analytical Data | SM |
|---|---|---|---|
| 1 | (racemic) 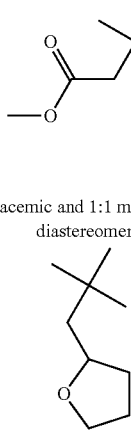 | NMR Spectrum: (DMSO-$d_6$) 1.47 (m, 1H), 1.66 (m, 2H), 1.85 (m, 1H), 2.30 (m, 2H), 2.88 (m, 3H), 3.29 (m, 1H), 3.62 (s, 3H), 4.87 (s, 2H), 6.61 (t, 1H), 6.79 (d, 1H), 6.98 (t, 1H), 7.18 (d, 1H), 7.40 (d, 2H), 7.92 (d, 2H), 9.57 (s, 1H); Mass Spectrum: M + H⁺368. | |
| 2 | (racemic and 1:1 mixture of diastereomers) 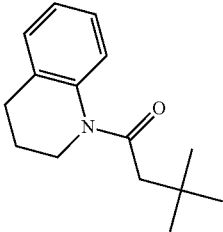 | NMR Spectrum: (CDC13) 1.42 (m, 1H), 1.88 (m, 3H), 2.39 (m, 3H), 2.93 (m, 4H), 3.67 and 3.99 (m, 1H), 3.80 (m, 2H), 6.78 (m, 2H), 7.02 (t, 1H), 7.28 (m, 3H), 7.72 (s, 1H), 7.77 (d, 2H); Mass Spectrum: M + H⁺ 380. | |
| 3 | 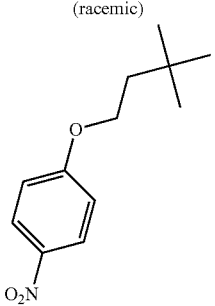 | NMR Spectrum: (DMSO-$d_6$) 1.48 (m, 2H), 1.68 (m, 1H), 1.80 (m, 1H), 1.90 (t, 2H), 2.15 (t, 1H), 2.22 (t, 1H), 2.72 (m, 2H), 2.82 (m, 1H), 2.90 (s, 2H), 3.73 (m, 2H), 4.86 (s, 2H), 6.60 (t, 1H), 6.78 (d, 1H), 6.97 (t, 1H), 7.14 (m, 4H), 7.36 (d, 2H), 7.57 (m, 1H), 7.91 (d, 2H), 9.56 (s, 1H); Mass Spectrum: M + H⁺ 469. | Method 73 |
| 4 | (racemic) 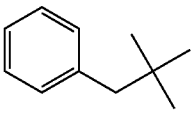 | Mass Spectrum: M + H⁺461 | CAS no. 13288-06-7 J. Prakt. Chem., 1881, 242 |
| 5 | | Mass Spectrum: M + H⁺366 | |
| 6 | (racemic) | Mass Spectrum: M + H⁺386 | |

TABLE 8-continued

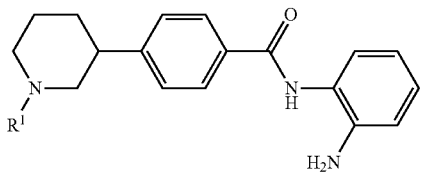

| Note | R¹ | Analytical Data | SM |
|---|---|---|---|
| 7 | (racemic) benzyl-O-CH2CH2-C(CH3)2-CH2- | Mass Spectrum: M + H⁺458 | |
| 8 | (racemic) 4-(diethylamino)phenyl-C(O)-CH2-C(CH3)3 | Mass Spectrum: M + H⁺485 | |
| 9 | (racemic) 4-HO-phenyl-O-CH2CH2-C(CH3)3 | Mass Spectrum: M + H⁺432 | |
| 10 | (racemic) 1,2,5-thiadiazol-3-yl-CH2-C(CH3)3 | Mass Spectrum: M + H⁺394 | CAS no. 53012-70-7 J. Het. Chem. 1984, 1157 |
| 11 | (racemic) naphthalen-2-yl-CH(OH)-C(CH3)3 | Mass Spectrum: M + H⁺466 | |
| 12 | (racemic) (CH3)2C=CH-CH2CH2-C(CH3)3 | Mass Spectrum: M + H⁺378 | |
| 13 | (racemic) 4-(AcNH)-phenyl-O-CH2CH2-C(CH3)3 | Mass Spectrum: M + H⁺473 | CAS no 57011-90-2 Justus Liebigs Ann. Chem. 1899, 287 DE 85988 |
| 14 | (racemic) EtO-CH2CH2-C(CH3)3 | Mass Spectrum: M + H⁺368 | |

TABLE 8-continued

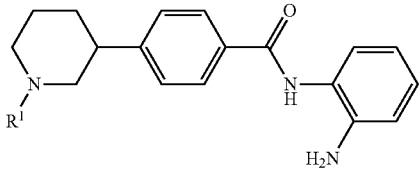

| Note | R¹ | Analytical Data | SM |
|---|---|---|---|
| 15 | (racemic) [tetrahydropyran-2-ylmethyl-neopentyl group] | Mass Spectrum: M + H⁺ 394 | |

EXAMPLE 24

Using an analogous procedure to that described in Example 19, N-(2-aminophenyl)-4-piperazin-1-ylbenzamide (Example 16) was reacted to give the compounds described in Table 9.

Preparation of the Starting Materials

The starting materials for the above examples are either commercially available or are readily prepared by standard methods from known materials. For example the following

TABLE 9

| Note | R¹ | Analytical Data | SM |
|---|---|---|---|
| 1 | [2-fluorophenyl-NH-C(O)-CH₂-C(CH₃)₃ group] | MR Spectrum: (CDCl₃) 2.62 (t, 2H), 2.78 (m, 6H), 3.45 (m, 4H), 6.83 (m, 2H), 7.07 (m, 3H), 7.26 (s, 1H), 7.31 (d, 1H), 7.74 (s, 1H), 7.84 (d, 2H), 7.96 (d, 2H), 8.41 (t, 1H), 11.07 (s, 1H); Mass Spectrum: M + H⁺ 462. | |
| 2 | [methyl ester-CH₂-C(CH₃)₃ group] | NMR Spectrum: (CDCl₃) 2.74 (m, 4H), 3.29 (s, 2H), 3.37 (m, 4H), 3.74 (s, 3H), 6.71 (m, 2H), 6.90 (d, 2H), 7.06 (t, 1H), 7.28 (d, 1H), 7.77 (s, 1H), 7.80 (d, 2H); Mass Spectrum: M + H⁺ 369. | |
| 3 | [benzyl-C(CH₃)₃ group] | NMR Spectrum: (CDCl₃) 2.61 (m, 4H), 3.33 (m, 4H), 3.57 (s, 2H), 6.81 (m, 4H), 6.91 (m, 2H), 7.06 (m, 2H), 7.34 (m, 3H), 7.72 (s, 1H), 7.80 (d, 2H); Mass Spectrum: M + H⁺ 387. | |
| 4 | [4-(diethylamino)phenyl-C(O)-CH₂-C(CH₃)₃ group] | NMR Spectrum: (CDCl₃) 1.21 (t, 6H), 2.77 (4H), 3.43 (m, 10H), 3.78 (s, 2H), 6.62 (d, 2H), 6.83 (m, 2H), 6.93 (d, 2H), 7.07 (t, 1H), 7.30 (d, 1H), 7.69 (s, 1H), 7.81 (d, 2H), 7.93 (d, 2H); Mass Spectrum: M + H⁺ 486. | | reactions are illustrations but not limitations of the preparation of some of the starting materials used in the above reactions.

Method 1

N-(2-t-Butoxycarbonylaminophenyl)-4-pyridin-4-ylbenzamide

N-(2-t-Butoxycarbonylaminophenyl)-4-bromobenzamide (Method 14; 136 mg, 0.33 mmol), pyridine-4-boronic acid (48 mg, 0.39 mmol), tetrakis(triphenylphosphine) palladium (5 mg, 0.005 mmol), THF (2 ml) and a saturated aqueous solution of sodium hydrogen carbonate (2 ml) were stirred at 55° C. under an atmosphere of argon for 96 hours. The cooled mixture was partitioned between ethyl acetate and water. The organics were washed with brine, dried over magnesium sulfate, filtered and evaporated, to give the title compound (103 mg, 80%), which was used without further purification; Mass Spectrum: M+H$^+$ 390.

Method 2

N-(2-t-Butoxycarbonylaminophenyl)-4-quinolin-8-ylbenzamide

N-(2-t-Butoxycarbonylaminophenyl)-4-bromobenzamide (Method 14; 200 mg, 0.5 mmol), 8-quinoline boronic acid (104 mg, 0.6 mmol), tetrakis(triphenylphosphine)palladium (8 mg, 0.007 mmol), 1,2-dimethoxyethane (3 ml) and a saturated aqueous solution of sodium hydrogen carbonate (3 ml) were stirred at 80° C. under an atmosphere of argon for 20 hours. The mixture was allowed to cool before being partitioned between ethyl acetate and water. The organics were washed with brine, dried over magnesium sulfate, filtered and evaporated. The resultant residue was purified by flash column chromatography, eluting with methanol/dichloromethane (0-10%), to give the title compound (201 mg, 84%); NMR Spectrum: (DMSO-d$_6$): 1.47 (s, 9H), 7.20 (m, 2H), 7.60 (m, 4H), 7.73 (t, 1H), 7.84 (t, 3H), 8.06 (d, 2H), 8.47 (d, 1H), 8.68 (s, 1H), 8.93 (m, 1H), 9.91 (s, 1H), Mass Spectrum: M+H$^+$: 440.

Method 3

N-(2-t-Butoxycarbonylaminophenyl)-4-pyridin-3-ylbenzamide

The title compound was prepared using an analogous procedure of Method 2 and used without further purification; Mass Spectrum: M+H$^+$ 390.

Method 4

N-(2-t-Butoxycarbonylaminophenyl)-4-pyridin-2-ylbenzamide

N-(2-t-Butoxycarbonylaminophenyl)-4-(4,4,5,5-tetramethyl-1,3,2-dioxaborolan-2-yl)benzamide (Method 13; 132 mg, 0.3 mmol), 2-bromopyridine (40 mg, 0.25 mmol), tetrakis(triphenylphosphine)palladium (4 mg, 0.004 mmol), 1,2-dimethyoxyethane (1.5 ml) and a saturated aqueous solution of sodium hydrogen carbonate (1.5 ml) were stirred at 80-85° C. under an atmosphere of argon for 24 hours. The mixture was allowed to cool before being partitioned between ethyl acetate and water. The organics were separated, washed with brine, dried over magnesium sulfate, filtered and evaporated to yield the title compound (86 mg, 74%) which was used in the next reaction without further purification; Mass Spectrum: M+H$^+$ 390.

Method 5-12

Using an analogous procedure to that described in Method 4, the N-(2-t-butoxycarbonylaminophenyl)-4-(4,4,5,5-tetramethyl-1,3,2-dioxaborolan-2-yl)benzamide starting material was reacted with the appropriate bromo compound to give the compounds described in Table 10. Where required, the crude residues were purified by flash column chromatography, eluting with methanol/dichloromethane (1:10).

TABLE 10

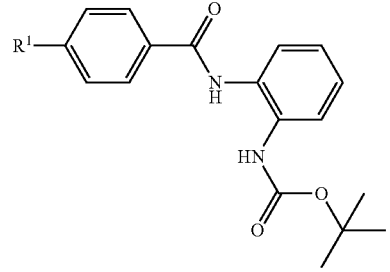

| Method | R$^1$ | Analytical Data | SM |
|---|---|---|---|
| 5 | 6-(methoxy)-1,2-pyrazin-3-yl | NMR Spectrum: (DMSO-d$_6$) 1.44 (s, 9H), 4.09 (s, 3H), 7.14 (m, 2H), 7.34 (d, 1H), 7.57 (t, 2H), 8.09 (d, 2H), 8.22 (d, 2H), 8.26 (d, 1H); Mass Spectrum: M + H$^+$421. | Meth 13 |
| 6 | furan-3-yl | Mass Spectrum: (M + H$^+$ -tBu) 323. | Meth 13 |
| 7 | 2-methylpridin-4-yl | NMR Spectrum: (DMSO-d$_6$) 1.46 (s, 9H), 2.57 (s, 3H), 7.20 (m, 2H), 7.59 (m, 3H), 7.69 (s, 1H), 7.98 (d, 2H), 8.10 (d, 2H), 8.56 (d, 1H), 8.67 (s, 1H), 9.92 (s, 1H); Mass Spectrum: M + H$^+$404. | Meth 13 |

TABLE 10-continued

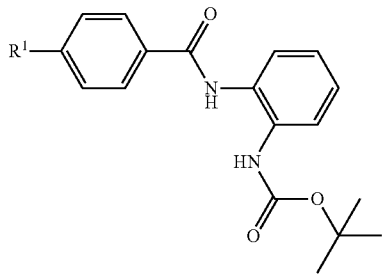

| Method | R¹ | Analytical Data | SM |
|---|---|---|---|
| 8 | 2-fluoropyridin-4-yl | NMR Spectrum: (DMSO-d$_6$) 1.46 (s, 9H), 7.20 (m, 2H), 7.57 (m, 2H), 7.65 (s, 1H), 7.81 (m, 1H), 8.06 (d, 2H), 8.12 (d, 2H), 8.37 (d, 1H), 8.68 (s, 1H), 9.94 (s, 1H); Mass Spectrum: (M + H⁺-Boc) 308. | Meth 13 |
| 9 | thiazol-2-yl | Mass Spectrum: (M + H⁺ -tBu) 340. | Meth 13 |
| 10 | 2-amino-pyrimidn-6-yl | Mass Spectrum: (M + Na⁺) 428. | Meth 13 |
| 11 | pyrimidin-6-yl | Mass Spectrum: (M + H⁺ -tBu) 335. | Meth 13 |
| 12 | 2-chloro-pyrimidin-6-yl | NMR Spectrum: (DMSO-d$_6$) 1.46 (s, 9H), 7.23 (m, 2H), 7.57 (t, 2H), 8.15 (d, 2H), 8.29 (d, 1H), 8.38 (d, 2H), 8.73 (br, 1H), 8.91 (d, 1H), 10.00 (s, 1H); Mass Spectrum: (M + H⁺-tBu) 369. | Meth 13 |

Method 13

N-(2-t-Butoxycarbonylaminophenyl)-4-(4,4,5,5-tetramethyl-1,3,2-dioxaborolan-2-yl)benzamide N-(2-t-Butoxycarbonylaminophenyl)-4-bromobenzamide (Method 14; 3.0 g, 7.7 mmol) was added to a solution of bis-pinacolato diboron (2.3 g, 9.2 mmol), 1,1-bis(diphenylphosphino)ferrocenedichloropalladium (II) chloride (157 mg, 0.19 mmol) and potassium acetate (2.3 g, 23 mmol) in DMF (48 ml) at 80° C. under an atmosphere of argon for 20 hours. The mixture was allowed to cool and the solvent removed in vacuo. The residue was partitioned between ethyl acetate and water. The organics were washed with brine, dried over magnesium sulphate and evaporated to give the title compound (3.9 g, quantitative), which was used without further purification; NMR Spectrum: (DMSO-d$_6$) 1.14 (s, 6H), 1.31 (s, 9H), 1.43 (s, 6H), 7.16 (m, 2H), 7.52 (m, 2H), 7.79 (d, 2H), 7.95 (d, 2H), 8.66 (s, 1H), 9.86 (s, 1H); Mass Spectrum: (M+H⁺-Boc) 383.

Method 14

N-(2-t-Butoxycarbonylaminophenyl)-4-bromobenzamide 4-(4,6-Dimethoxy-1,3,5-triazinyl-2-yl)-4-methylmorpholinium chloride (Method 18; 5.4 g, 19.4 mmol) was added to a solution of 4-bromobenzoic acid (3.5 g, 17.4 mmol) and 1-(N-t-butoxycarbonylamino)-2-aminobenzene (Method 17; 4.3 g, 20.9 mmol) in DMF (100 ml) and stirred at ambient temperature for 20 hours. The reaction mixture was partitioned between water and ethyl acetate. The organics were washed with a saturated aqueous solution of sodium hydrogen carbonate, water, 1M aqueous hydrochloric acid, water and brine, before being dried over magnesium sulfate. The organics were then evaporated to give the title compound (7.1 g, quantitative), which was used without further purification. NMR Spectrum: (DMSO-d$_6$): 1.45 (s, 9H), 7.18 (m, 2H), 7.54 (m, 2H), 7.76 (d, 2H), 7.90 (d, 2H), 8.63 (s, 1H), 9.86 (s, 1H); Mass Spectrum: (M+H⁺-Boc) 291.

Method 15

N-(2-t-Butoxycarbonylaminophenyl)-4-(1-t-butoxycarbonylpiperidin-4-yl)benzamide 1-(N-t-Butoxycarbonylamino)-2-aminobenzene (Method 17, 3.1 g, 14.7 mmol) was added to a stirred solution of 4-(1-t-butoxycarbonylpiperidin-4-yl)benzoic acid (4.1 g, 13.4 mmol) in DMF (50 ml) and the mixture stirred at ambient temperature for 10 minutes. 4-(4,6-dimethoxy-1,3,5-triazinyl-2-yl)-4-methylmorpholinium chloride (Method 18, 4.45 g, 16.1 mmol) was added and the mixture stirred at ambient temperature for 24 hours. The solvent was evaporated and the residue was dissolved in ethyl acetate (100 ml) and washed with water. The organics were dried over magnesium sulfate, filtered and evaporated. The resultant gum was purified by flash chromatography using 1% methanol/dichloromethane to give the title compound as a foam (5.44 g, 82%); NMR Spectrum: (DMSO-d$_6$) 1.41 (s, 9H), 1.43 (s, 9H), 1.54 (m, 2H), 1.77 (m, 2H), 2.79 (m, 3H), 4.08 (m, 2H), 7.15 (m, 2H), 7.40 (d, 2H), 7.52 (m, 2H), 7.87 (d, 2H), 8.60 (br, 1H), 9.74 (br, 1H), Mass Spectrum: (M+H⁺-Boc) 396.

Method 16

N-(2-t-Butoxycarbonylaminophenyl)-4-(1-methylpiperazin-4-yl)benzamide 4-(1-Methylpiperazin-4-yl)benzoic acid (250 mg, 1.13 mmol) and 1-(N-t-butoxycarbonylamino)-2-aminobenzene (Method 17, 331 mg, 1.59 mmol) were dissolved in DMF (3 ml). 4-(4,6-dimethoxy-1,3,5-triazinyl-2-yl)-4-methylmorpholinium chloride (Method 18, 313 mg, 1.13 mmol) was added and the resulting solution was stirred for 20 hours at ambient temperature. The solution was poured into water and extracted several times with ethyl acetate. The combined organic extracts were dried over magnesium sulfate and evaporated. The residue was purified by flash chromatography (eluting with 99:1→9:1 dichloromethane:methanol) to afford the title compound as a colourless gum which crystallised on trituration (240 mg, 52%); Mass Spectrum: M+H$^+$ 411.

Method 17

1-(N-t-Butoxycarbonylamino)-2-aminobenzene

The title compound was prepared according to the literature method described in Seto, C, T.; Mathias, J. P.; Whitesides, G. M.; *J. Am. Chem. Soc.*, 1993, 115, 1321-1329.

Method 18

4-(4,6-Dimethoxy-1,3,5-triazinyl-2-yl)-4-methylmorpholinium chloride 4-(4,6-Dimethoxy-1,3,5-triazinyl-2-yl)-4-methylmorpholinium chloride was prepared according to the literature procedure described in Kunishima, M., Kawachi, C., Morita, J., Terao, K., Iwasaki, F., Tani, S., *Tetrahedron*, 1999, 55, 13159-13170.

Method 19

N-(2-Aminophenyl)-4-[2-(3-morpholinoaminopropyl)-pyrimidin-6-yl]benzamide trihydrochloride N-(2-t-Butoxyaminophenyl)-4-[2-(3-morpholinoaminopropyl)-pyrimidin-6-yl]benzamide (Method 20, 64 mg, 0.120 mmol) was suspended in 1,4 dioxane (1.5 ml) and a 4M solution of hydrogen chloride in 1,4-dioxane (1 ml) added. The reaction mixture was stirred at ambient temperature for 64 hours. The reaction mixture was diluted with diethyl ether, and the resultant precipitate was collected by filtration, washed with diethyl ether and air dried, to yield the title compound (as its hydrochloride salt) as an off white solid (62 mg, 95%); Mass Spectrum: M+H$^+$ 433.

Method 20

N-(2-t-Butoxyaminophenyl)-4-[2-(3-morpholinoaminopropyl)-pyrimidin-6-yl]benzamide N-(2-t-Butoxyaminophenyl)-4-(2-methylsulfonyl-pyrimidin-6-yl)benzamide (Method 21, 62.5 mg, 0.133 mmol) was dissolved in a mixture of THF (2 ml) and N,N-dimethylacetamide (2 ml) and N-(3-aminopropyl)morpholine (60 µl 0.411 mmol) added. The reaction mixture was heated to 50° C. and stirred for 2 hours. The reaction mixture was then cooled and solvents removed under reduced pressure. The resultant oil was purified by elution through silica with a 5% methanol in dichloromethane, to yield the title compound as a colourless solid (65 mg, 92%); NMR Spectrum: (DMSO-d$_6$) 1.45 (s, 9H), 1.74 (m, 2H), 2.37 (m, 6H), 3.40 (br, 2H), 3.59 (m, 4H), 7.20 (m, 2H), 7.23 (d, 1H), 7.34 (t, 1H), 7.57 (d, 1H), 8.08 (d, 2H), 8.26 (d, 2H), 8.40 (m, 1H), 8.72 (s, 1H), 9.94 (s, 1H); Mass Spectrum: M+H$^+$ 534.

Method 21

N-(2-t-Butoxyaminophenyl)-4-(2-methylsulfonyl-pyrimidin-6-yl)benzamide

N-(2-t-Butoxyaminophenyl)-4-(2-thiomethyl-pyrimidin-6-yl)benzamide (Method 22, 140 mg, 0.32 mmol) was dissolved in methanol (8 ml) and a small amount of ethyl acetate, followed by a solution of Oxone® (630 mg, 1.02 mmol) in water (4 ml). The resultant suspension was stirred at ambient temperature for 1 hour before being partitioned between ethyl acetate and a mixture of water and saturated sodium bicarbonate. The organic phase was separated and the aqueous phase extracted with further aliquots of ethyl acetate. The combined organic extracts were washed with brine and dried over magnesium sulfate. Evaporation to dryness afforded the title compound as an off white powder (126 mg, 84%); NMR Spectrum: (DMSO-d$_6$) 1.45 (s, 9H), 3.54 (s, 3H), 7.20 (m, 2H), 7.57 (t, 2H), 8.18 (d, 2H), 8.48 (d, 2H), 8.54 (s, 1H), 8.73 (s, 1H), 9.20 (d, 1H), 10.02 (s, 1H); Mass Spectrum: (M+H$^+$-Boc) 369.

Method 22

N-(2-t-Butoxyaminophenyl)-4-(2-thiomethyl-pyrimidin-6-yl)benzamide

4-Iodo-2-methylthiopyrimidine (Method 23, 360 mg, 1.43 mmol) was reacted with N-(2-t-butoxycarbonylaminophenyl)-4-(4,4,5,5-tetramethyl-1,3,2-dioxaborolan-2-yl)benzamide (Method 13, 631 mg, 1.44 mmol) in an analogous manner to that described in Method 4 to yield the crude title compound. This was purified by elution through silica with a solution of ethyl acetate in isohexane (25% to 50% (v/v)) to afford the pure title compound as a pale yellow foam (306 mg, 49%); NMR Spectrum: (DMSO-d$_6$) 1.45 (s, 9H), 2.63 (s, 3H), 7.20 (m, 2H), 7.57 (t, 2H), 7.91 (d, 1H), 8.13 (d, 2H), 8.37 (d, 2H), 8.72 (s, 1H), 8.77 (d, 1H), 9.97 (s, 1H); Mass Spectrum: (M+H$^+$-tBu) 381.

Method 23

4-Iodo-2-methylthiopyrimidine

4-Chloro-2-methylthiopyrimidine (5 g, 31.15 mmol) was added dropwise to a cooled 57% aqueous hydriodic acid solution (0° C.). Stirring was continued at 0° C. for 30 minutes, before warming to ambient temperature and stirring for 24 hours. Aqueous sodium bicarbonate was then carefully added and the resultant suspension basified to pH 9 by addition of sodium carbonate. The mixture was extracted with ethyl acetate and the extracts dried over magnesium sulfate and concentrated by reduced pressure. The resultant solid was dissolved in boiling isohexane and cooled by refridgeration overnight. The resultant solid was filtered and dried to afford the title compound as colourless needles (5.4 g, 69%); NMR Spectrum: (CDCl$_3$) 2.55 (s, 3H), 7.40 (d, 1H), 7.98 (d, 1H); Mass Spectrum: M+H$^+$ 253.

Method 24

N-(2-Aminophenyl)-4-[2-(3-morpholinoaminoethyl)-pyrimidin-6-yl]benzamide trihydrochloride N-(2-t-Butoxyaminophenyl)-4-[2-(3-morpholinoaminoethyl)-pyrimidin-6-yl]benzamide (Method 25, 59 mg, 0.113 mmol) was reacted in an analogous manner to that described for Method 19 to yield the title compound (as its hydrochloride salt) as a beige solid (56 mg, 94%); Mass Spectrum: M+H$^+$ 419.

Method 25

N-(2-t-Butoxyaminophenyl)-4-[2-(3-morpholinoaminoethyl)-pyrimidin-6-yl]benzamide N-(2-t-Butoxyaminophenyl)-4-(2-methylsulfonyl-pyrimidin-6-yl)benzamide (Method 21, 62.5 mg, 0.133 mmol) was reacted with N-(2-aminoethyl)morpholine (60 μl, 0.457 mmol) in an analogous manner to that described in method 20 to yield the title compound as a pale yellow solid (66 mg, 96%); NMR Spectrum: (DMSO-$d_6$) 1.46 (s, 9H), 2.45 (brm, 4H), 3.30 (m, 2H), 3.50 (brm, 2H), 3.58 (m, 4H), 7.14 (t, 1H), 7.17 (m, 1H), 7.22 (m, 1H), 7.25 (d, 1H), 7.57 (d, 2H), 8.09 (d, 2H), 8.27 (d, 2H), 8.42 (d, 1H), 8.73 (s, 1H), 9.94 (s, 1H); Mass Spectrum: M+H$^+$ 519.

Method 29

N-(2-t-butoxycarbonylaminophenyl)-4-{2-[(3-piperidin-1-ylpropyl)amino]pyrimidin-4-yl}benzamide To a 24 mm×150 mm pyrex tube, charged with 3-aminopropylpiperidine (73 mg, 0.51 mmol), was added a solution of N-(2-t-butoxycarbonylaminophenyl)-4-(2-chloropyrimidin-4-yl)benzamide (Method 52, 85 mg, 0.20 mmol) in N,N-dimethylacetamide (4.6 ml). The reaction mixture was then heated to 50° C. and stirred for 16 hours, before being evaporated to dryness. The resultant residue was purified by flash chromatography, on silica (10 g), eluting with methanol/dichloromethane (5-15%), to give the title compound (48 mg, 45%); Mass Spectrum: M+H$^+$ 531.

Method 30-36

Using an analogous procedure to that described in Method 29, the N-(2-t-butoxycarbonylaminophenyl)-4-(2-chloropyrimidin-4-yl)benzamide starting material (Method 52) was reacted with the appropriate amine to give the compounds described in Table 11. Where required, the crude residues were purified by flash column chromatography, on silica (10 g), eluting with methanol/dichloromethane (5-15%).

TABLE 11

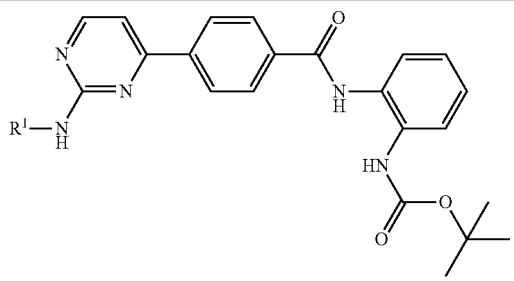

| Method | R$^1$ | Analytical Data | SM |
|---|---|---|---|
| 30 | (imidazolyl-butyl-t-Bu) | Mass Spectrum: M + H$^+$ 514. | |
| 31 | (4-methylpiperazinyl-butyl-t-Bu) | Mass Spectrum: M + H$^+$ 546. | |
| 32 | (diethylamino-pentyl-t-Bu) | Mass Spectrum: M + H$^+$ 533. | |
| 33 | (diethylamino-propyl-t-Bu) | Mass Spectrum: M + H$^+$ 505. | |
| 34 | (pyridin-3-yl-ethyl-t-Bu) | Mass Spectrum: M + H$^+$ 497. | |

TABLE 11-continued

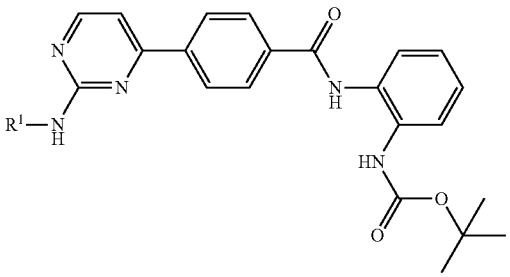

| Method | R¹ | Analytical Data | SM |
|---|---|---|---|
| 35 | (piperidine-CH2CH2-C(CH3)2-CH2-) | Mass Spectrum: M + H⁺ 517. | |
| 36 | (CH3-O-CH2CH2-C(CH3)2-CH2-) | Mass Spectrum: M + H⁺ 478. | Meth 52 |

Method 37

N-(2-t-butoxycarbonylaminophenyl)-4-[2-(3-morpholin-4-ylpropoxy)pyridin-4-yl]benzamide To a suspension of sodium hydride in tetrahydrofuran (1 ml) was added, dropwise, via syringe, a solution of 3-N-morpholinopropanol (147 mg, 1.01 mmol). The reaction mixture was stirred, under an argon atmosphere, for 30 minutes, then added, via cannula, to a solution of N-(2-t-butoxycarbonylaminophenyl)-2-fluoropyridin-4-ylbenzamide (Method 8, 119 mg, 0.29 mmol) in tetrahydrofuran (2 ml). The mixture was then stirred, under an argon atmosphere, for 2 hours at ambient temperature, before being heated to 50° C. and stirred for a further 5.5 hours. The reaction mixture was allowed to cool before being partitioned between ethyl acetate and water. The organics were separated and aqueous extracted further with ethyl acetate. The combined organic layers were then combined, washed with brine, dried over magnesium sulfate, filtered and evaporated. The resultant residue was purified by flash chromatography, on silica (20 g), eluting with methanol/dichloromethane (0-10%), to give the title compound (70 mg, 45%); NMR Spectrum: (DMSO-d₆) 1.46 (s, 9H), 1.92 (m, 2H), 2.38 (m, 4H), 2.45 (m, 2H), 3.59 (t, 4H), 4.36 (t, 2H), 7.20 (m, 3H), 7.39 (dd, 1H), 7.57 (d, 2H), 7.97 (d, 2H), 8.08 (d, 2H), 8.26 (d, 1H), 8.67 (s, 1H), 9.91 (s, 1H); Mass Spectrum: M+H⁺ 533.

Method 38

N-(2-t-butoxycarbonylaminophenyl)-4-(6-methylpyridin-3-yl)benzamide

Using an analogous procedure to that described in Method 4, N-(2-t-butoxycarbonylaminophenyl)-4-(4,4,5,5-tetramethyl-1,3,2-dioxaborolan-2-yl)benzamide (Method 13, 1.20 g, 2.74 mmol) was reacted with 2-methyl-5-bromopyridine (505 mg, 2.94 mmol). The crude residue was purified by flash chromatography on silica (90 g), eluting with ethyl acetate/isohexane (40-100%) to give the title compound (504 mg, 46%); NMR Spectrum: (DMSO-d₆) 1.46 (s, 9H), 2.51 (s, 3H), 7.19 (m, 2H), 7.40 (d, 1H), 7.58 (m, 2H), 7.91 (d, 2H), 8.08, (d, 3H), 8.66 (s, 1H), 8.86 (d, 1H), 9.89 (s, 1H); Mass Spectrum: M+H⁺ 404.

Method 39

N-(2-t-butoxycarbonylaminophenyl)-4-{2-[(3-piperidin-1-ylpropyl)amino]thieno[3,2-d]pyrimidin-4-yl}benzamide A solution of 3-aminopropylpiperidine (60 μl, 0.38 mmol) and N-(2-t-butoxycarbonylaminophenyl)-4-[2-(methylsulfonyl)thieno[3,2-d]pyrimidin-4-yl]benzamide (Method 54, 81 mg, 0.15 mmol) in N,N-dimethylacetamide was heated first to 50° C. for 23 hours and then further heated to 75° C. for a period of 16 hours. The reaction mixture was evaporated to dryness and the crude residue purified by flash chromatography, on silica (10 g), eluting with methanol/dichloromethane (0-15%) to give the title compound (23 mg, 26%); Mass Spectrum: M+H$^+$ 587.

Method 40

N-(2-t-butoxycarbonylaminophenyl)-4-thieno[3,2-d]pyrimidin-4-ylbenzamide

Using an analogous procedure to that described in Method 4, 4-chlorothieno[3,2-d]pyrimidine (538 mg, 3.15 mmol) was reacted with N-(2-t-butoxycarbonylaminophenyl)-4-(4,4,5,5-tetramethyl-1,3,2-dioxaborolan-2-yl)benzamide (Method 13, 1.53 g, 3.50 mmol). The crude residue was purified by flash chromatography, on silica, eluting with ethyl acetate/hexane (25-75%) to give the title compound (1.08 g, 69%); NMR Spectrum: (DMSO-d$_6$) 1.47 (s, 9H), 7.21 (m, 2H), 7.57 (t, 2H), 7.79 (d, 1H), 8.23 (d, 2H), 8.34 (d, 2H), 8.64 (d, 1H), 8.75 (s, 1H), 9.35 (s, 1H), 10.03 (s, 1H); Mass Spectrum: M+H$^+$ 447.

Method 41

N-(2-aminophenyl)-4-{2-[(3-piperidin-1-ylpropyl)amino]pyrimidin-5-yl}benzamide To a solution of N-(2-t-butoxycarbonylaminophenyl)-4-(2-chloropyrimidin-5-yl)benzamide (Method 53, 80 mg, 0.19 mmol) in N,N-dimethylacetamide (3.5 ml) was added 3-aminopropylpiperidine (108 mg 0.76 mmol). The reaction mixture was stirred at 50° C. for 20 hours, before being allowed to cool. The reaction mixture was partitioned between water and ethyl acetate, before being filtered under gravity, through a Varian Chem Elut (CE1010) diatomaceous earth column. The resulting solution was then concentrated under reduced pressure and purified by flash column chromatography, eluting with methanol/dichloromethane (0-20%), to give the title compound, which was used without further purification; Mass Spectrum: M+H$^+$ 531.

Method 42-43

Using an analogous procedure to that described in method 41, the N-(2-t-butoxycarbonylaminophenyl)-4-(2-chloropyrimidin-5-yl)benzamide (Method 53) was reacted with the appropriate amine to give the compounds described in Table 12. Where required, the crude residues were purified by flash column chromatography, on silica (10 g), eluting with methanol/dichloromethane (0-20%).

TABLE 12

| Method | R$^1$ | Analytical Data SM |
|---|---|---|
| 42 | *N-methylpiperazinyl-propyl group* | Mass Spectrum: M + H$^+$ 546 |
| 43 | *morpholinyl-propyl group* | Mass Spectrum: M + H$^+$ 533. |

Method 44

N-(2-t-butoxycarbonylaminophenyl)-3-fluoro-4-pyridin-3-ylbenzamide t-Butyl 2-[(4-bromo-3-fluorobenzoyl)amino]phenylcarbamate (Method 63, 205 mg, 0.5 mmol), 3-pyridine boronic acid (74 mg, 0.6 mmol), tetrakis(triphenylphosphine) palladium (104 mg, 0.09 mmol), 1,2-dimethoxyethane (3 ml) and a saturated aqueous solution of sodium hydrogen carbonate (3 ml) were stirred at 80° C. under an atmosphere of argon for 48 hours. The cooled mixture was partitioned between ethyl acetate and water. The aqueous layer was removed using Varian Chem Elut column (CE1010) and the resulting solution was then concentrated under reduced pressure and purified by flash column chromatography, eluting with ethyl acetate/isohexane (25-75%), to give the title compound (186 mg, 91%). Mass Spectrum: M+H$^+$ 408.

Method 45

N-(2-t-butoxycarbonylaminophenyl)-4-[2-(2-pyrrolidin-1-ylethoxy)pyrimidin-5-yl]benzamide Using an analogous procedure to that described in Method 44, N-(2-t-butoxycarbonylaminophenyl)-4-(4,4,5,5-tetramethyl-1,3,2-dioxaborolan-2-yl)benzamide (Method 13, 219 mg, 0.5 mmol) was reacted with 5-bromo-2-(2-pyrrolidin-1-ylethoxy)pyrimidine (Method 64, 136 mg, 0.5 mmol) to give the title compound (71 mg; 28%). Mass Spectrum: M+H$^+$ 504.

Method 46-50

Using an analogous procedure to that described in Example 1, the appropriate N-(2-t-butoxycarbonylaminophenyl)benzamide starting material was reacted to give the compounds described in Table 13, as their hydrochloride salt.

TABLE 13

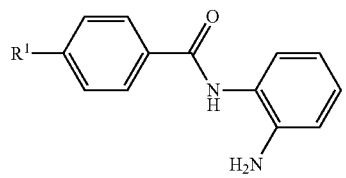

| Method | R¹ | Analytical Data | SM |
|---|---|---|---|
| 46 | (morpholine-propyl-NH-pyridine-tBu) | Mass Spectrum: M + H⁺ 432. | Meth 56 |
| 47 | (methylpurine-tBu) | Used without further purification. | Meth 57 |
| 48 | (piperazine-pyrimidine-tBu) | Mass Spectrum: M + H⁺ 375. | Meth 58 |
| 49 | (bis-ethylamino-triazine-tBu) | Mass Spectrum: M + H⁺ 378 | Meth 59 |
| 50 | (N-methylpiperazine-pyrimidine-tBu) | Mass Spectrum: M + H⁺ 389 | Meth 60 |

Method 51

N-(2-t-butoxycarbonylaminophenyl)-4-[5-(piperidin-1-ylmethyl)-1,3-thiazol-2-yl]benzamide Using an analogous procedure to that described in Method 44, N-(2-t-butoxycarbonylaminophenyl)-4-(4,4,5,5-tetramethyl-1,3,2-dioxaborolan-2-yl)benzamide (Method 13, 219 mg, 0.5 mmol) was reacted with 1-[(2-chloro-1,3-thiazol-5-yl)methyl]piperidine (108 mg, 0.5 mmol) to give the title compound (271 mg, >100%) which was carried through the next step; Mass Spectrum: M+H⁺ 493.

Method 52

N-(2-t-butoxycarbonylaminophenyl)-4-(2-chloropyrimidin-4-yl)benzamide

Using an analogous procedure to that described in Method 4, N-(2-t-butoxycarbonylaminophenyl)-4-(4,4,5,5-tetramethyl-1,3,2-dioxaborolan-2-yl)benzamide (Method 13, 3.9 g, 8.9 mmol) was reacted with 2,4-dichloropyrimidine (3.06 g, 20.5 mmol). The crude residue was purified by flash chromatography on silica, eluting with ethyl acetate/isohexane (1:1) to give the title compound (1.2 g, 32%); NMR Spectrum: (DMSO-d₆) 1.45 (s, 9H), 7.23 (m, 2H), 7.57 (t, 2H), 8.15 (d, 2H), 8.29 (d, 1H), 8.38 (d, 2H), 8.73 (s, 1H), 8.91 (d, 1H), 10.00 (s, 1H); Mass Spectrum: M−H⁻ 423.

Method 53

N-(2-t-butoxycarbonylaminophenyl)-4-(2-chloropyrimidin-5-yl)benzamide

N-(2-t-butoxycarbonylaminophenyl)-4-(4,4,5,5-tetramethyl-1,3,2-dioxaborolan-2-yl)benzamide (Method 13, 4.0 g, 9.12 mmol), 5-bromo-2-chloropyrimidine (1.76 g, 9.12 mmol), tetrakis(triphenylphosphine) palladium (527 mg, 0.46 mmol), 1,2-dimethoxyethane (40 ml) and a saturated aqueous solution of sodium hydrogen carbonate (40 ml) were stirred at 80° C. under an atmosphere of argon for 18 hours. The cooled mixture was concentrated under reduced pressure. The residue was then stirred with ethyl acetate for 1 hour and the resultant solid collected by suction filtration and dried to give the title compound (2.38 g; 61%); NMR Spectrum: (DMSO-$d_6$) 1.47 (s, 9H), 7.20 (m, 2H), 7.58 (d, 2H), 8.02 (d, 2H), 8.11 (d, 2H), 8.66 (s, 1H), 9.23 (s, 2H), 10.93 (s, 1H); Mass Spectrum: M+H$^+$-$^t$Bu 369.

Method 54

N-(2-t-butoxycarbonylaminophenyl)-4-[2-(methylsulfonyl)thieno[3,2-d]pyrimidin-4-yl]benzamide To a cooled (0° C.) solution of N-(2-t-butoxycarbonylaminophenyl)-4-[2-(methylthio)thieno[3,2-d]pyrimidin-4-yl] benzamide (Method 55, 960 mg, 1.95 mg) in DMF (40 ml), was added meta-chloroperbenzoic acid (57%, 630 mg, 2.08 mmol) and the reaction mixture stirred, allowing warming to ambient temperature. After 3 hours a further portion of meta-chloroperbenzoic acid (70%, 589 mg, 2.40 mmol) was added and stirring continued for 2 hours. The reaction mixture was then carefully poured into aqueous sodium metabisulfite solution (0.25M, 100 ml), before addition of ethyl acetate (100 ml). The insoluble material was removed by filtration and dried in vacuo to yield the title compound (586 mg, 57%); NMR Spectrum: (DMSO-$d_6$) 1.46 (s, 9H), 3.57 (s, 3H), 7.18 (t, 1H), 7.24 (t, 1H), 7.59 (m, 2H), 8.00 (d, 1H), 8.27 (d, 2H), 8.41 (d, 2H), 8.75 (s, 1H), 8.90 (d, 1H), 10.07 (s, 1H); Mass Spectrum: M+Na$^+$ 547.

Method 55-59

Using an analogous procedure to that described in Method 4, N-(2-t-butoxycarbonylaminophenyl)-4-(4,4,5,5-tetramethyl-1,3,2-dioxaborolan-2-yl)benzamide (Method 13) was reacted with the appropriate halide to give the compounds described in Table 14. Where appropriate compounds were filtered from reaction mixtures following partitioning or if required, the crude residues were purified by flash column chromatography, on silica eluting with methanol/dichloromethane (0-20%).

TABLE 14

| Method | R$^1$ | Analytical Data | SM |
|---|---|---|---|
| 55 | SMe (thieno[3,2-d]pyrimidine with t-butyl) | NMR Spectrum: (DMSO-$d_6$) 1.46 (s, 9H), 2.67 (s, 3H), 7.17 (t, 1H), 7.23 (t, 1H), 7.59 (t, 2H), 7.65 (d, 1H), 8.22 (d, 2H), 8.30 (d, 2H), 8.59 (d, 1H), 8.75 (brs, 1H), 10.03 (s, 1H); Mass Spectrum: M + H$^+$ 493. | [CAS 176530-47-5] |
| 56 | morpholine-propyl-NH-pyridine with t-butyl | NMR Spectrum: (DMSO-$d_6$) 1.46 (s, 9H), 1.72 (m, 2H), 2.37 (m, 6H), 3.33 (m, 2H), 3.58 (t, 4H), 6.62 (t, 1H), 6.77 (s, 1H), 6.83 (d, 1H), 7.19 (m, 2H), 7.56 (d, 2H), 7.81 (d, 2H), 8.07 (m, 3H), 8.66 (s, 1H), 9.89 (s, 1H); Mass Spectrum: M + H$^+$ 532. | Meth 61 |
| 57 | N-methylpurine with t-butyl | NMR Spectrum: (DMSO-$d_6$) 1.47 (s, 9H), 3.92 (s, 3H), 7.18 (m, 2H), 7.59 (m, 2H), 8.18 (d, 2H), 8.70 (s, 1H), 9.00 (d, 2H), 9.06 (s, 1H), 9.97 (brs, 1H); Mass Spectrum: M + H$^+$ 445. | [CAS 2346-74-9] |

TABLE 14-continued

| Method | R¹ | Analytical Data | SM |
|---|---|---|---|
| 58 | (piperazinyl-tert-butylpyrazine) | Mass Spectrum: M + H⁺ -Boc 376. | [CAS 61655-58-1] |
| 59 | (bis-ethylamino-tert-butyltriazine) | Mass Spectrum: M + H⁺ 479. | [CAS 122-34-9] |

Method 60

N-(2-t-Butoxycarbonylaminophenyl)-4-[2-(4-methylpiperazin-1-yl)pyrimidin-4-yl]benzamide Using an analogous procedure to that described in Method 41, the N-(2-t-butoxycarbonylaminophenyl)-4-(2-chloropyrimidin-4-yl)benzamide (Method 52, 59 mg, 0.14 mmol) was reacted with 1-methylpiperazine (77 mg, 0.69 mmol) and residue purified by flash chromatography eluting with methanol/dichloromethane (0-20%) to give the title compound (48 mg, 71%); Mass Spectrum: M+H⁺ 489.

Method 61

4-Iodo-N-(3-morpholin-4-ylpropyl)pyridin-2-amine

A solution of 4-iodo-2-fluoropyridine (2.32 g, 10.00 mmol) and N-(3-aminopropyl)morpholine (4.2 ml, 26.00 mmol) in N,N-dimethylacetamide (30 ml) was heated to 100° C. for 20 hours before being concentrated in vacuo, to afford the crude title compound which was used without any further purification; Mass Spectrum: M+H⁺ 348.

Method 62

N-(2-aminophenyl)-4-[2-(methylsulfonyl)pyrimidin-4-yl]benzamide

Using an analogous procedure to that described in Example 1, N-(2-t-butoxycarbonylaminophenyl)-4-[2-(methylsulfonyl)pyrimidin-4-yl]benzamide (Method 21, 1.097 g, 2.34 mmol) was reacted to give the title compound as its hydrochloride salt (1.01 g, 98%); NMR Spectrum: (DMSO-d₆) 3.53 (s, 3H), 7.31 (m, 3H), 7.52 (d, 1H), 8.30 (d, 2H), 8.48 (d, 2H), 8.53 (d, 1H), 9.20 (d, 1H), 10.56 (s, 1H); Mass Spectrum: M+H⁺ 369.

Method 63 t-Butyl 2-[(4-bromo-3-fluorobenzoyl)amino]phenylcarbamate 1-(N-t-butoxycarbonylamino)-2-aminobenzene (Method 17, 1.25 g, 6 mmol) was reacted with 4-bromo-3-fluorobenzoic acid (1.1 g, 5.0 mmol) in an analogous manner to that described in Method 16 to give the title compound, which was used without further purification; Mass Spectrum: (M+H⁺-Boc) 311.

Method 64

5-bromo-2-(2-pyrrolidin-1-ylethoxy)pyrimidine

To a solution of N-2-hydroxyethylpyrrolidine (0.9 ml, 7.71 mmol) and 5-bromo-2-chloropyrimidine (1.2 g, 6.20 mmol), in DMF (7 ml), was added sodium hydride (60% in mineral oil, 0.35 g, 8.75 mmol). The mixture was stirred, under argon, at ambient temperature for 1 hour, before being heated to 90° C. and stirred for a further hour. The reaction mixture was then partitioned between ethyl acetate and water. The organics were separated, dried over magnesium sulfate and evaporated to dryness. The resultant oil was purified by flash chromatography on silica, eluting with an increasing gradient of methanol in dichloromethane (which contained 1% aqueous ammonia solution, 0.88 M) to give the title compound (640 mg, 38%); NMR Spectrum: (CDCl$_3$) 1.76 (m, 4H), 2.39 (m, 4H), 3.90 (t, 2H), 4.48 (t, 2H), 8.50 (s, 2H); Mass Spectrum: M+H$^+$ 272.

Method 65-66

Using an analogous procedure to that described in Method 39, N-(2-t-butoxycarbonylaminophenyl)-4-[2-(methylsulfonyl)thieno[3,2-d]pyrimidin-4-yl]benzamide (Method 54) was reacted with the appropriate amine to give the compounds described in Table 15. The resultant residues, where required, were purified by flash chromatography on silica, eluting with methanol/dichloromethane (0-15%).

TABLE 15

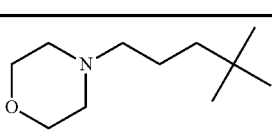

| Method | R$^1$ | Analytical Data | SM |
|---|---|---|---|
| 65 | | Used without further purification. | |
| 66 | | Mass Spectrum: M + H$^+$ 573. | |

Method 67

[2-(4-{[(2-t-butoxycarbonylaminophenyl)amino]carbonyl}phenyl)-1,3-thiazol-5-yl]methyl cyclohexylcarbamate Using an analogous procedure to that described in Method 4, N-(2-t-butoxycarbonylaminophenyl)-4-(4,4,5,5-tetramethyl-1,3,2-dioxaborolan-2-yl)benzamide (Method 13, 219 mg, 0.5 mmol) was reacted with (2-chloro-1,3-thiazol-5-yl) methyl cyclohexylcarbamate (138 mg, 0.5 mmol). The crude residue was stirred in ethyl acetate for 16 hours before being filtered, mixed with water and the aqueous removed using a Varian Chem Elut Column (CE1010). The resulting solution was concentrated and purified by flash chromatography on silica, eluting with methanol/dichloromethane (0-30%) to give the title compound; Mass Spectrum: M+H$^+$ 551.

Method 68

N-(2-t-butoxycarbonylaminophenyl)-4-{5-[2-(methylthio)pyrimidin-4-yl]thien-2-yl}benzamide Using an analogous procedure to that described in Method 4, N-(2-t-butoxycarbonylaminophenyl)-4-(4,4,5,5-tetramethyl-1,3,2-dioxaborolan-2-yl)benzamide (Method 13, 219 mg, 0.5 mmol) was reacted with 4-(5-bromothien-2-yl)-2-(methylthio)pyrimidine (145 mg, 0.5 mmol). The crude residue stirred in ethyl acetate/water for 1 hour before being filtered, and the aqueous removed using a Varian Chem Elut Column (CE1010). The resulting solution was concentrated and recrystallised from methanol to give the title compound; Mass Spectrum: M+H$^+$-Boc 463.

Method 69

[2-(4-{[(2-t-butoxycarbonylaminophenyl)amino]carbonyl}phenyl)-1,3-thiazol-5-yl]methyl phenylcarbamate Using an analogous procedure to that described in Method 4, N-(2-t-butoxycarbonylaminophenyl)-4-(4,4,5,5-tetramethyl-1,3,2-dioxaborolan-2-yl)benzamide (Method 13, 219 mg, 0.5 mmol) was reacted with (2-chloro-1,3-thiazol-5-yl) methyl N-phenylcarbamate (136 mg, 0.5 mmol). The crude residue stirred in ethyl acetate/water for 16 hours before being filtered, and the aqueous removed using a Varian Chem Elut Column (CE1010). The resulting solution was concentrated and purified by flash chromatography on silica, eluting with methanol/dichloromethane (0-30%) to give the title compound; Mass Spectrum: M+H$^+$-Boc 489.

Method 70

[2-(4-{[(2-aminophenyl)amino]carbonyl}phenyl)-1,3-thiazol-5-yl]methyl phenylcarbamate Using an analogous procedure to that described in Example 12, the appropriate N-(2-t-butoxycarbonylaminophenyl)benzamide starting material was reacted to give the compound described in Table 16, as its hydrochloride salt.

TABLE 16

| Structure | Analytical Data | SM |
|---|---|---|
| 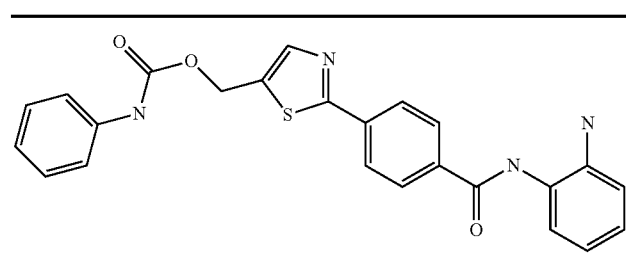 | Mass Spectrum: M + H$^+$ 445. | Meth 69 |

Method 71 t-Butyl 4-{4-[({2-[(t-butoxycarbonyl)amino]phenyl}amino)carbonyl]phenyl}-3,6-dihydropyridine-1(2H)-carboxylate A saturated solution of sodium hydrogen carbonate (3 ml) was added to a stirred solution of t-butyl 4-{[(trifluoromethyl)sulfonyl]oxy}-3,6-dihydropyridine-1(2H)-carboxylate (Method 72, 200 mg, 0.60 mmol) in 1,2-dimethoxyethane (3 ml). N-(2-t-butoxycarbonylaminophenyl)-4-(4,4,5,5-tetramethyl-1,3,2-dioxaborolan-2-yl)benzamide (Method 13) (318 mg, 0.72 mmol) was added followed by tetrakis(triphenylphosphine) palladium (100 mg, 0.09 mmol) and the mixture stirred at 80° C. for 18 hours. The cooled mixture was partitioned between ethyl acetate and water. The organic phase was separated, then washed with water and dried over magnesium sulfate, filtered and evaporated. The resultant residue was purified by flash column chromatography (eluting with 0-15% methanol in dichloromethane) to give the title compound (220 mg, 74%); NMR Spectrum: (DMSO-$d_6$) 1.42 (s, 9H), 1.43 (s, 9H), 2.48 (m, 2H), 3.55 (m, 2H), 4.02 (m, 2H), 6.31 (s, 1H), 7.17 (m, 2H), 7.52 (m, 2H), 7.58 (d, 2H), 7.92 (d, 2H), 8.62 (s, 1H), 9.79 (s, 1H); Mass Spectrum: M+H$^+$ 494.

Method 72 t-Butyl 4-{[(trifluoromethyl)sulfonyl]oxy}-3,6-dihydropyridine-1(2H)-carboxylate A 1.6 M solution of n-butyllithium in hexanes (6.9 ml, 11 mmol) was added to a stirred solution of diisopropylamine (1.5 ml, 11 mmol) in THF at −78° C. and the mixture stirred for 30 minutes. A solution of t-butyl 4-oxopiperidine-1-carboxylate (2.0 g, 10 mmol) in THF was added and after 20 minutes a solution of N-phenyl-bis(trifluoromethanesulfonimide) (3.9 g, 11 mmol) in THF was added. The mixture was stirred at ambient temperature overnight and the solvent evaporated. The resultant residue was partioned between diethyl ether and a 2M solution of aqueous sodium hydroxide, the organic layer separated, washed once with brine and dried over magnesium sulfate, filtered and evaporated to give the title compound (3.01 g, 83%); NMR Spectrum: (DMSO-$d_6$) 1.48 (s, 9H), 2.44 (m, 2H), 3.63 (t, 2H), 4.04 (d, 2H), 5.76 (s, 1H).

Method 73

1-Bromoacetyl-1,2,3,4-tetrahydroquinoline 1,2,3,4-tetrahydroquinoline (10 g, 75 mmol) was dissolved in benzene (40 ml) and cooled to 10° C. A solution of bromoacetyl bromide (16 g, 80 mmol) in benzene (40 ml) was added dropwise over 1 hour. The mixture was stirred for a further 15 minutes. A 2M aqueous solution of sodium hydroxide (500 ml) was added. The organic layer was separated, washed with water (100 ml), dried over magnesium sulfate and evaporated to afford the crude product as an oil. This was purified by distillation under reduced pressure followed by recrystallisation from 60-80 petroleum ether to afford the product as a colourless solid (12.5 g, 66%). Anal. Calc. for $C_{11}H_{12}ONBr$ gives C, 52.0%; H, 4.8%; N, 5.5%; Br, 31.4%; found C, 51.9%, 4.8%; N, 5.6%; Br, 30.9%.

Method 74-75

Using an analogous procedure to that described in Method 4, N-(2-t-Butoxycarbonylaminophenyl)-4-(4,4,5,5-tetramethyl-1,3,2-dioxaborolan-2-yl)benzamide (Method 13) was reacted with the requisite chloroheterocycle to give the compounds described in Table 17

TABLE 17

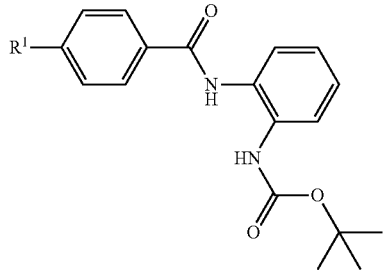

| Method | R$^1$ | Analytical Data | SM |
|---|---|---|---|
| 74 | 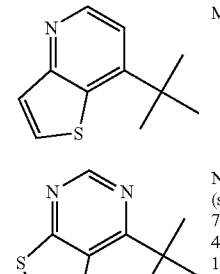 | Mass Spectrum: M + H$^+$ 446. | Meth 76 |
| 75 |  | NMR Spectrum: (DMSO-$d_6$) 1.47 (s, 9H), 7.21 (m, 2H), 7.58 (m, 2H), 7.78 (d, 1H), 8.12 (d, 1H), 8.19 (m, 4H), 8.71 (s, 1H), 9.23 (s, 1H), 10.01 (s, 1H); Mass Spectrum: M + H$^+$347. |  |

Method 76

7-chlorothieno[3,2-b]pyridine

Thieno[3,2-b]pyridin-7-ol (200 mg; 1.32 mmol) was added to thionyl chloride (1.57 g; 13.2 mmol), followed by a drop of DMF. The solution was stirred at 80° C. for 4 hours. The cooled solution was diluted with ethyl acetate and neutralised to pH 7 with a saturated solution of sodium hydrogen carbonate (25 ml). The organic layer was washed with brine, dried and concentrated to yield the title compound (112 mg; 50%); Mass Spectrum: M+H⁺ 170.

The invention claimed is:

1. A compound of the formula (I):

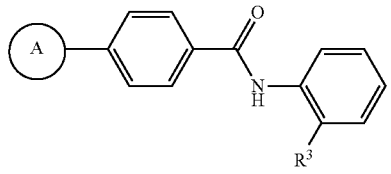

(I)

wherein:
Ring A is piperidinyl, wherein the nitrogen within the piperidinyl ring can be optionally substituted by K;
K is independently selected from $C_{1-8}$alkyl, $C_{2-8}$alkenyl, $C_{1-8}$alkanoyl, $C_{1-8}$alkylsulphonyl, $C_{1-8}$alkoxycarbonyl, carbamoyl, N—($C_{1-8}$alkyl)carbamoyl, N,N—($C_{1-8}$alkyl)carbamoyl, benzyloxycarbonyl, benzoyl, phenylsulphonyl, aryl, aryl$C_{1-6}$alkyl or (heterocyclic group)$C_{1-6}$alkyl; wherein K may be optionally substituted on carbon by one or more Q; and wherein if said heterocyclic group contains a —NH— moiety that nitrogen may be optionally substituted by hydrogen or $C_{1-6}$alkyl;
Q is halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, aryl, aryloxy, aryl $C_{1-6}$alkyl, aryl$C_{1-6}$alkoxy, heterocyclic group, (heterocyclic group)$C_{1-6}$alkyl, or (heterocyclic group)$C_{1-6}$alkoxy;
$R^3$ is amino or hydroxy;
or a pharmaceutically acceptable salt thereof.

2. A compound of the formula (I) or a pharmaceutically acceptable salt thereof according to claim 1 wherein $R^3$ is amino.

3. A process for preparing a compound of formula (I) or a pharmaceutically acceptable salt thereof, according to claim 1, which process comprises:
(a) reacting a compound of the formula (II)

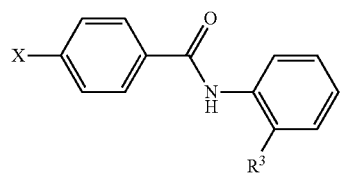

(II)

wherein X is a reactive group, with a compound of the formula (III)

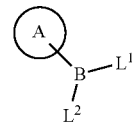

(III)

wherein $L^1$ and $L^2$ are ligands;
(b) reacting a compound of the formula (IV)

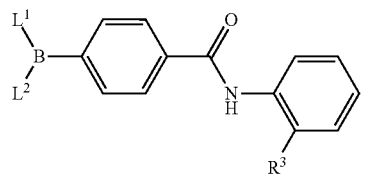

(IV)

wherein $L^1$ and $L^2$ are ligands, with a compound of the formula (V)

(V)

wherein X is a reactive group; or
(c) reacting, in the presence of 4-(4,6-dimethoxy-1,3,5-triazinyl-2-yl)-4-methylmorpholinium chloride, of a compound of the formula (VI)

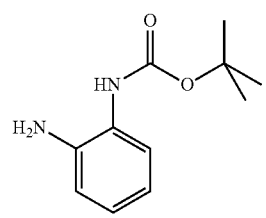

(VI)

with a compound of the formula (VII)

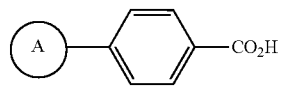

(VII)

and thereafter optionally:
i) converting a compound of the formula (I) into another compound of the formula (I); and/or
ii) removing any protecting groups.

4. A pharmaceutical composition which comprises a compound of the formula (I), or a pharmaceutically acceptable salt thereof, according to any one of claim 1 or 2 in association with a pharmaceutically-acceptable diluent or carrier.

5. A compound selected from any one of the following:

N-(2-Aminophenyl)-4-(1-methylpiperidin-4-yl)benzamide;

N-(2-Aminophenyl)-4-piperidin-4-ylbenzamide;

N-(2-aminophenyl)-4-piperidin-3-ylbenzamide;

4-(1-acetylpiperidin-4-yl)-N-(2-aminophenyl)benzamide;

N-(2-aminophenyl)-4-[1-(4-bromobenzoyl)piperidin-4-yl]benzamide;

or a pharmaceutically acceptable salt thereof.

* * * * *